(12) United States Patent
Drasler

(10) Patent No.: US 10,238,492 B2
(45) Date of Patent: Mar. 26, 2019

(54) PERIVALVULAR OCCLUSION DEVICE AND METHODS

(71) Applicant: William Joseph Drasler, Minnetonka, MN (US)

(72) Inventor: William Joseph Drasler, Minnetonka, MN (US)

(*) Notice: Subject to any disclaimer, the term of this patent is extended or adjusted under 35 U.S.C. 154(b) by 174 days.

(21) Appl. No.: 15/252,395

(22) Filed: Aug. 31, 2016

(65) Prior Publication Data

US 2018/0055627 A1  Mar. 1, 2018

(51) Int. Cl.
*A61F 2/24*  (2006.01)

(52) U.S. Cl.
CPC .......... *A61F 2/246* (2013.01); *A61F 2/2466* (2013.01); *A61F 2210/0014* (2013.01); *A61F 2250/0003* (2013.01)

(58) Field of Classification Search
CPC ............... A61F 2/246; A61F 2/2466; A61F 2250/0003; A61F 2210/0014; A61F 2/915; A61F 2/958; A61F 2/07; A61F 2/82; A61F 2/90; A61F 2/95; A61F 6/20–6/24; A61F 5/003–5/0046; A61B 17/12022; A61B 17/12109; A61B 17/12031; A61B 17/12036; A61B 2017/22067; A61B 2017/12054; A61M 25/1018; A61M 2025/1054; A61M 25/10
USPC ....................................................... 623/1.11
See application file for complete search history.

(56) References Cited

U.S. PATENT DOCUMENTS

| 5,181,921 | A | * | 1/1993 | Makita | A61B 17/12109 604/247 |
| 5,779,672 | A | * | 7/1998 | Dormandy, Jr. | A61B 17/12109 604/99.04 |
| 5,785,685 | A | * | 7/1998 | Kugler | A61M 25/1018 604/103.1 |
| 7,691,119 | B2 | * | 4/2010 | Farnan | A61F 2/86 606/159 |
| 9,855,086 | B2 | * | 1/2018 | Muller | A61B 17/8855 |
| 2012/0221089 | A1 | * | 8/2012 | Drasler | A61F 2/958 623/1.11 |
| 2013/0023980 | A1 | * | 1/2013 | Drasler | A61F 2/2412 623/1.26 |
| 2014/0074142 | A1 | * | 3/2014 | Khieu | A61F 5/003 606/192 |
| 2014/0172003 | A1 | * | 6/2014 | Goepfrich | A61M 29/02 606/192 |
| 2015/0173898 | A1 | * | 6/2015 | Drasler | A61F 2/2418 623/2.18 |

* cited by examiner

*Primary Examiner* — Todd J Scherbel
*Assistant Examiner* — Andrew Peter Restaino

(57) ABSTRACT

An occlusion device intended for blocking perivalvular leak channels that are found following heart valve implantation between the heart valve and the surrounding tissue. The occlusion device has a stent and a covering that is attached to the stent surface. A blocking fabric extends across the lumen of the stent to block blood flow. The stent pattern and wall structure provide for small radius of curvature bends to fill narrow channels that cause the perivalvular leaks.

13 Claims, 26 Drawing Sheets

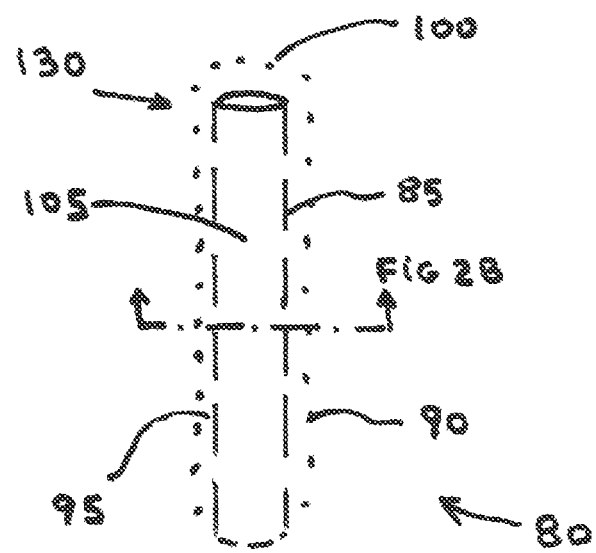

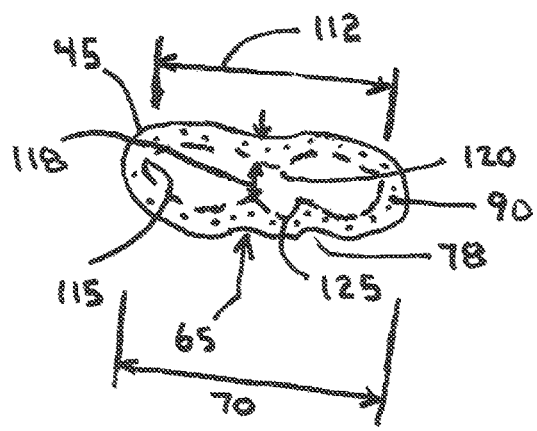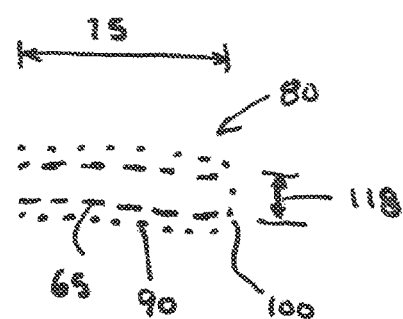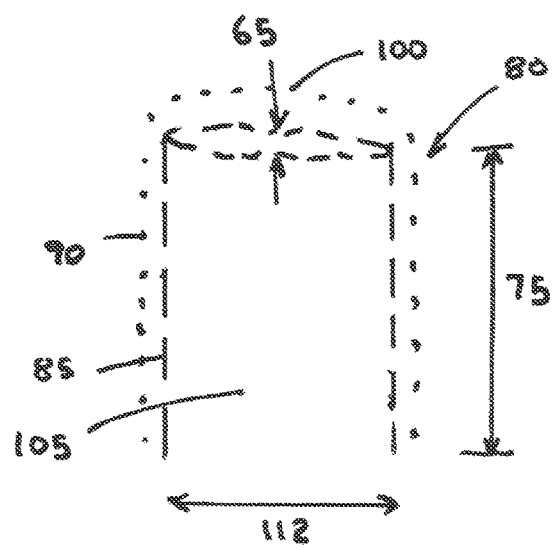

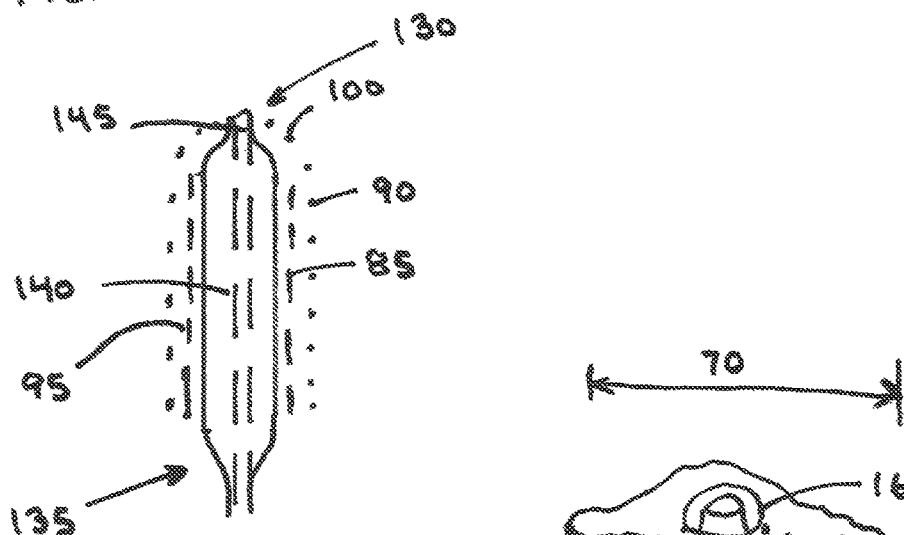
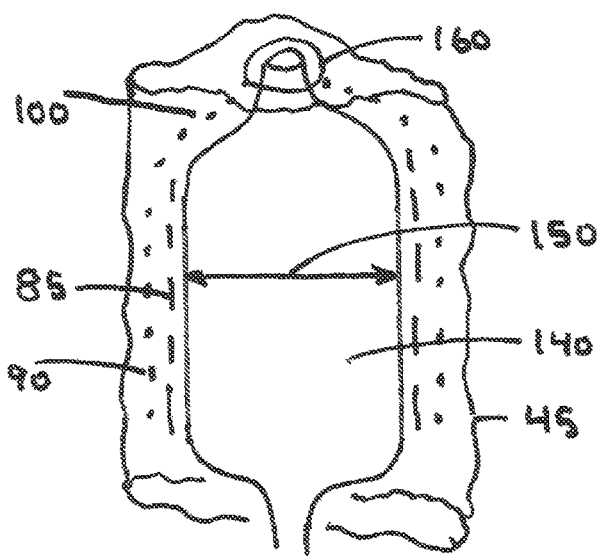
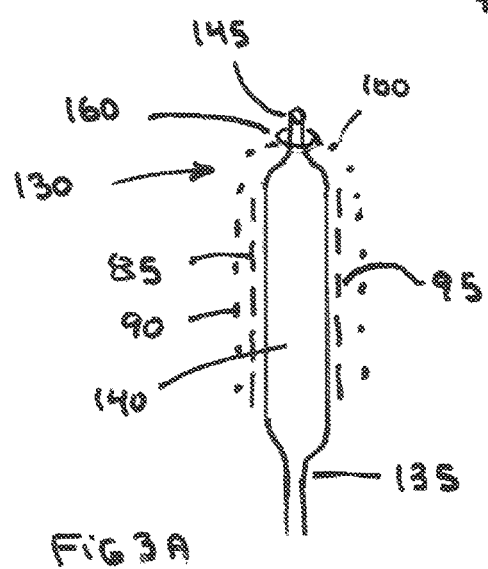

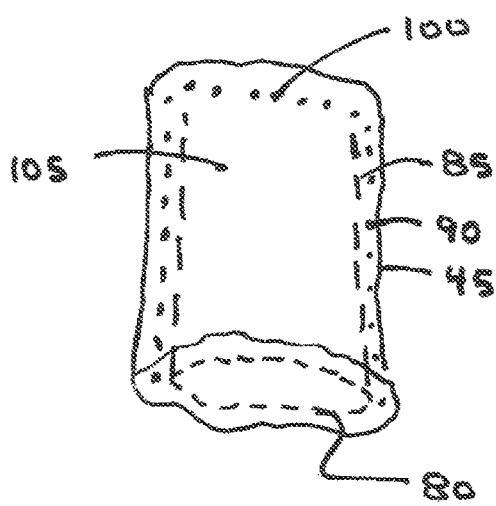
FIG. 3D
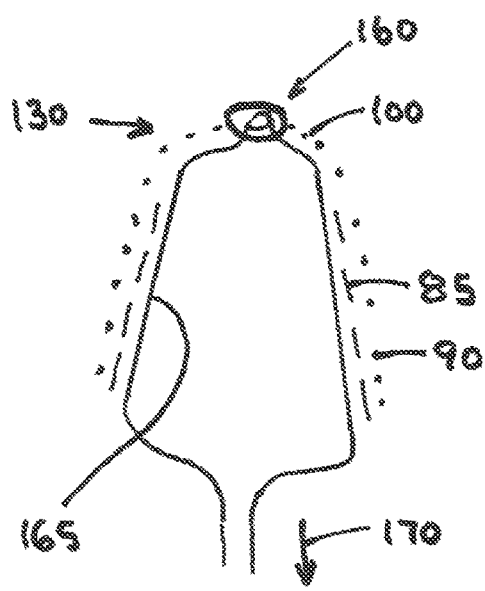
FIG 3F

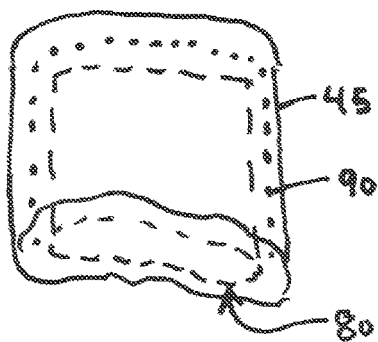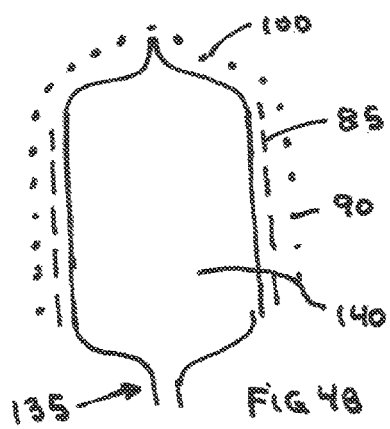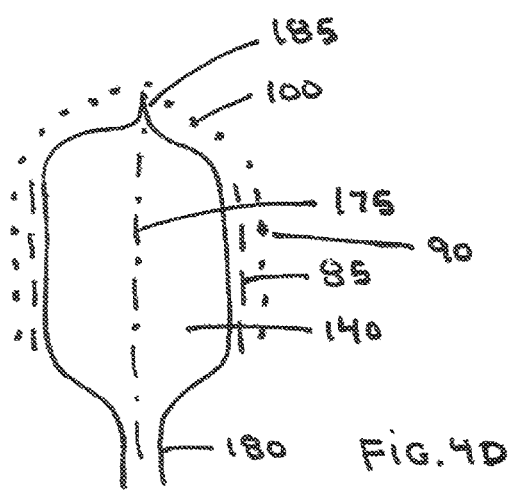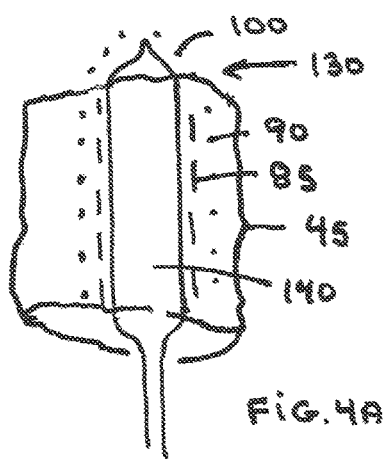

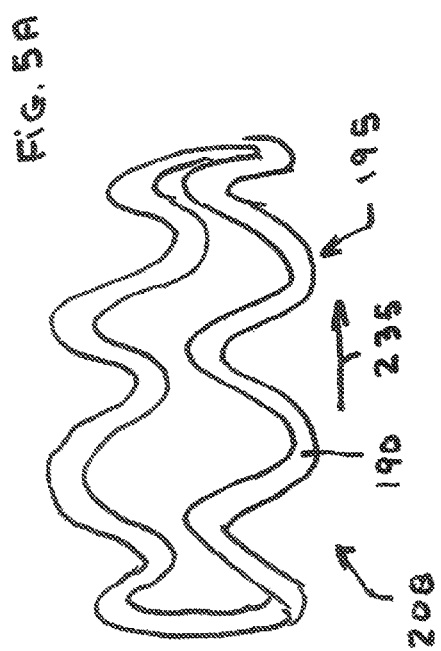
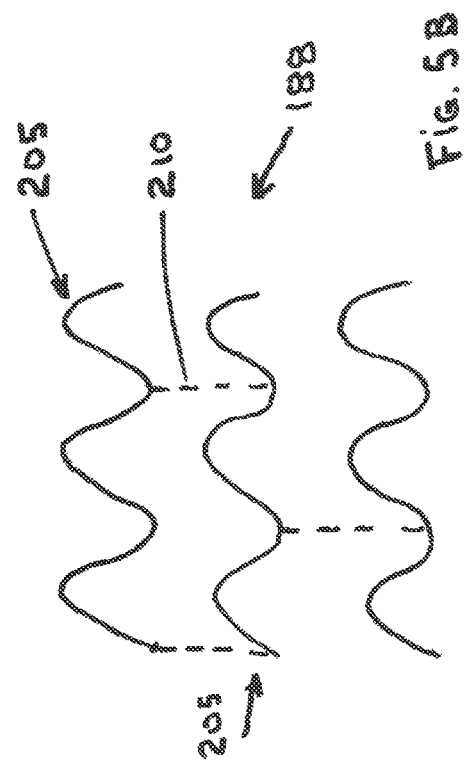

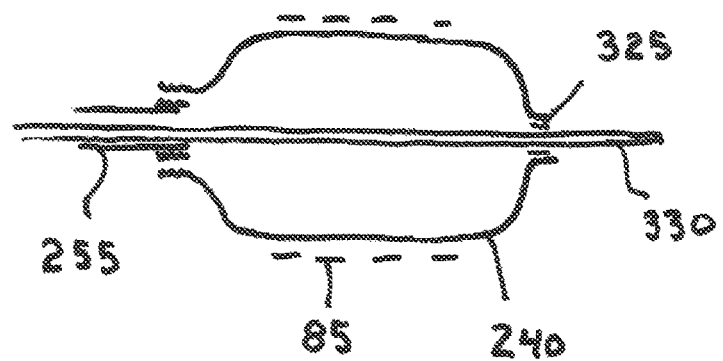

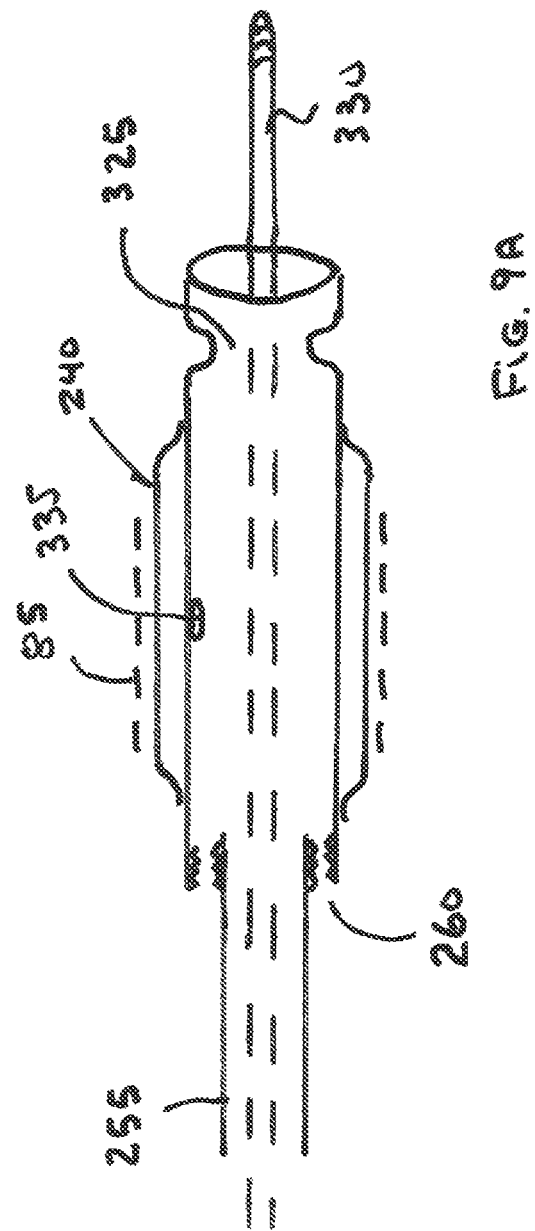

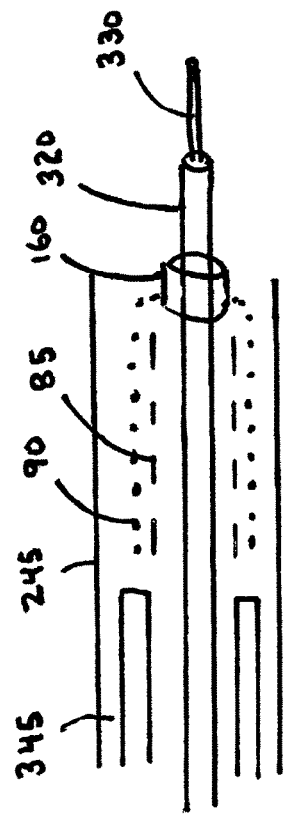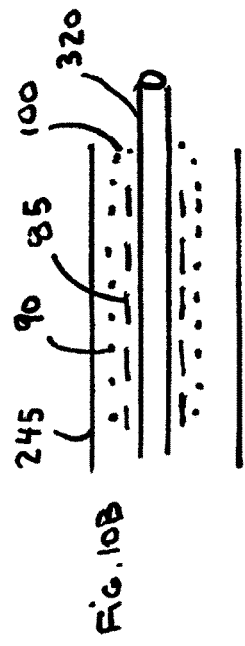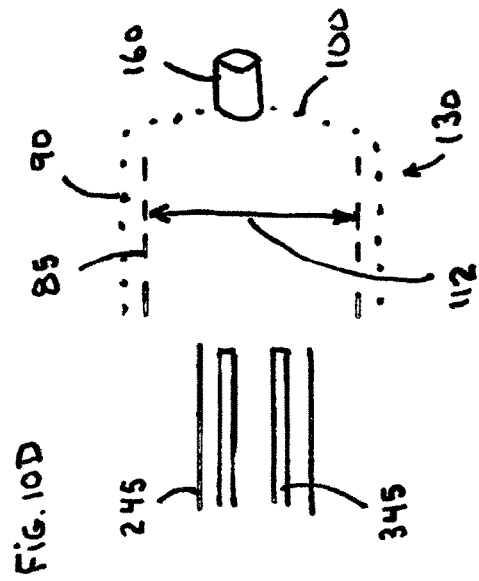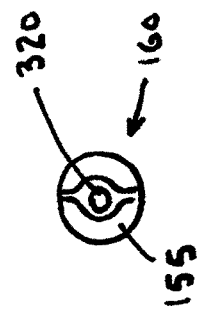

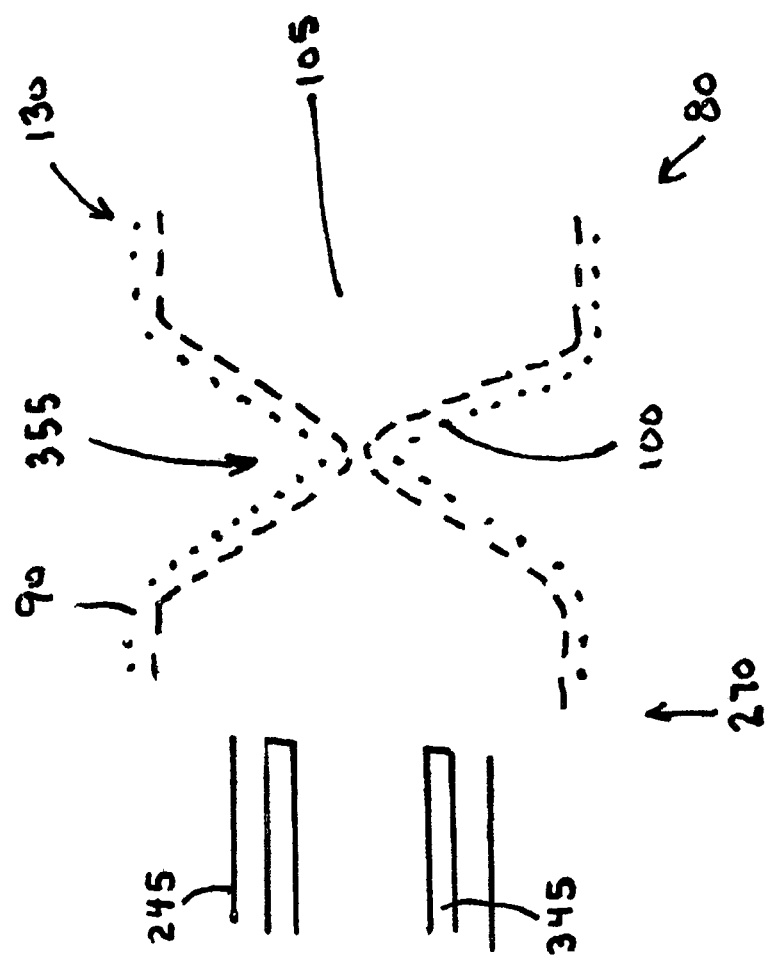

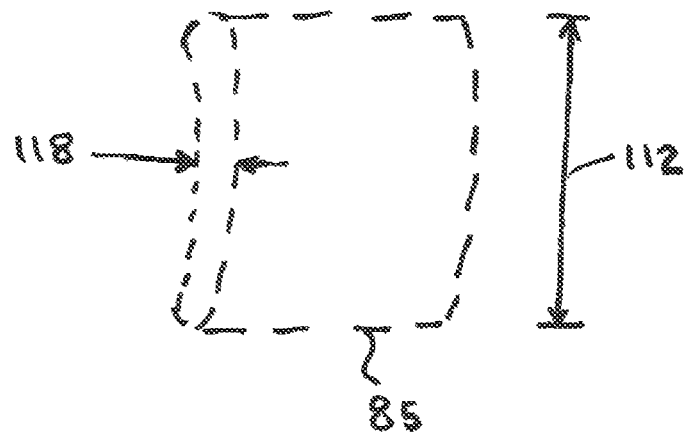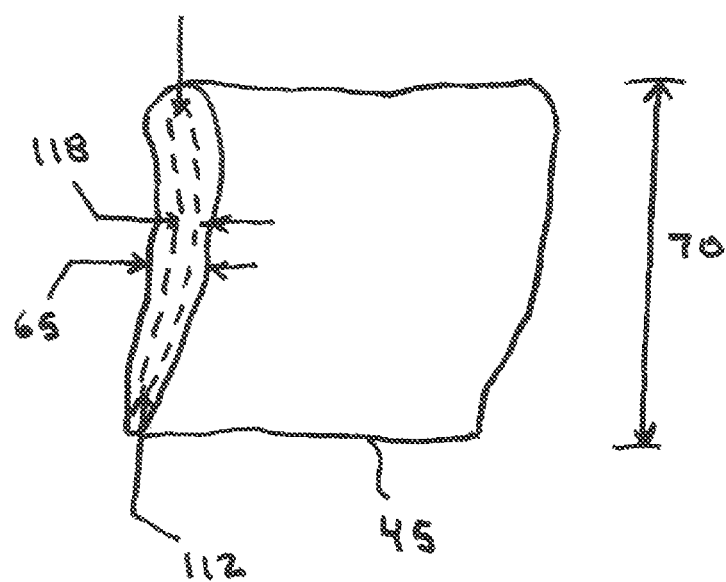

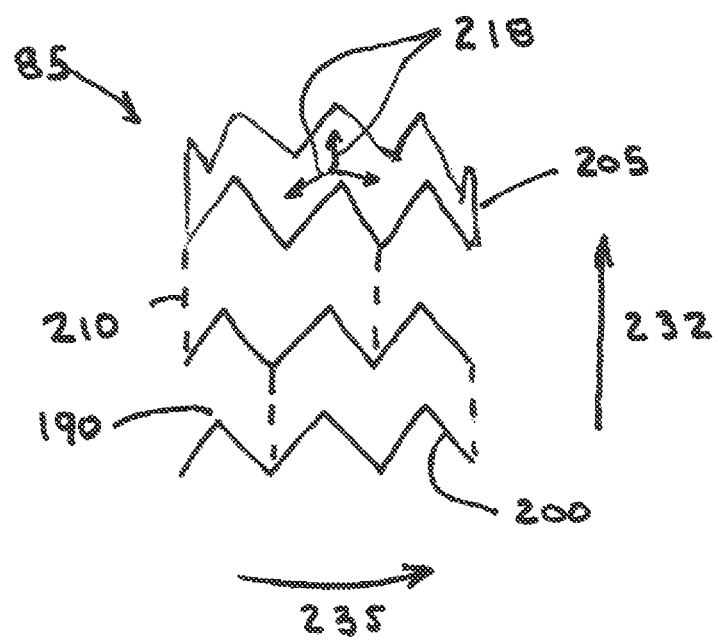

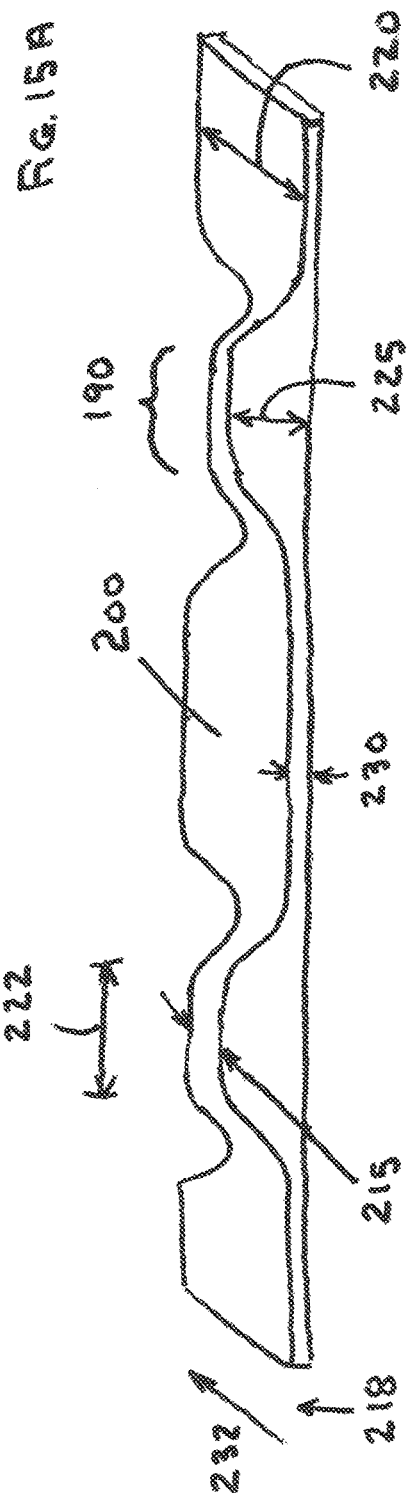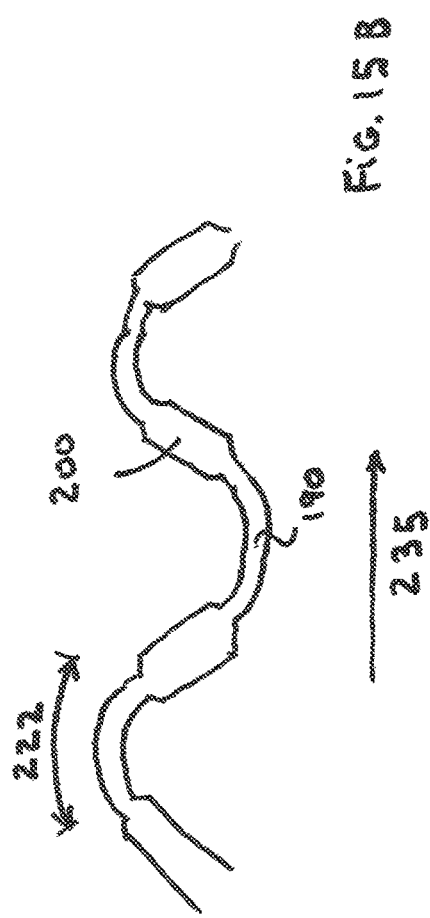

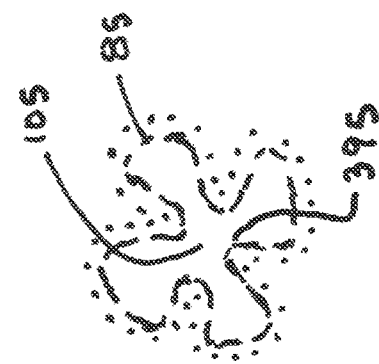
FIG. 17A  FIG. 17B
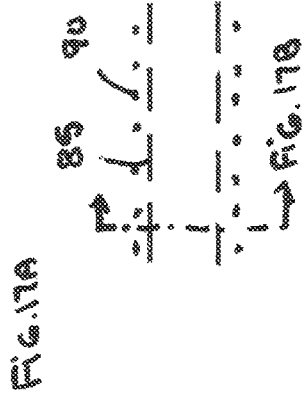
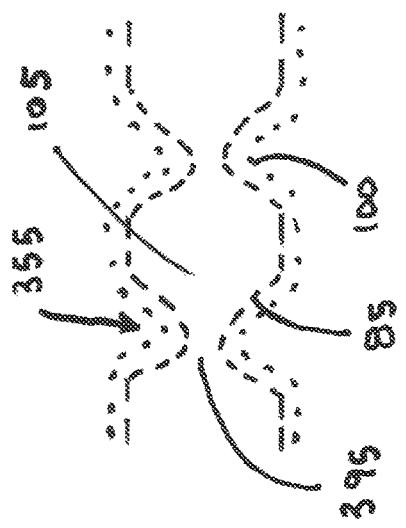
FIG. 17C  FIG. 17D

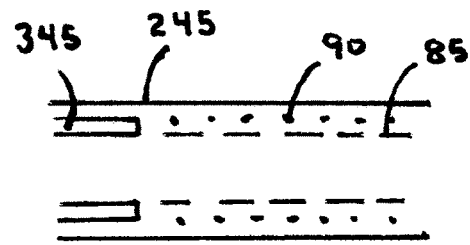
FIG. 19A
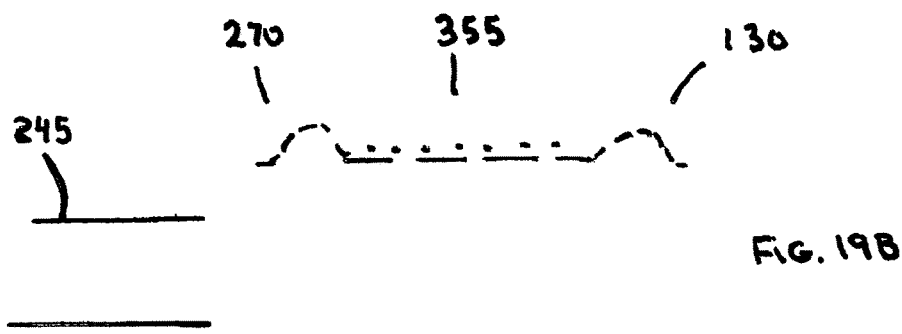
FIG. 19B
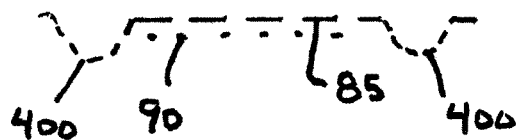
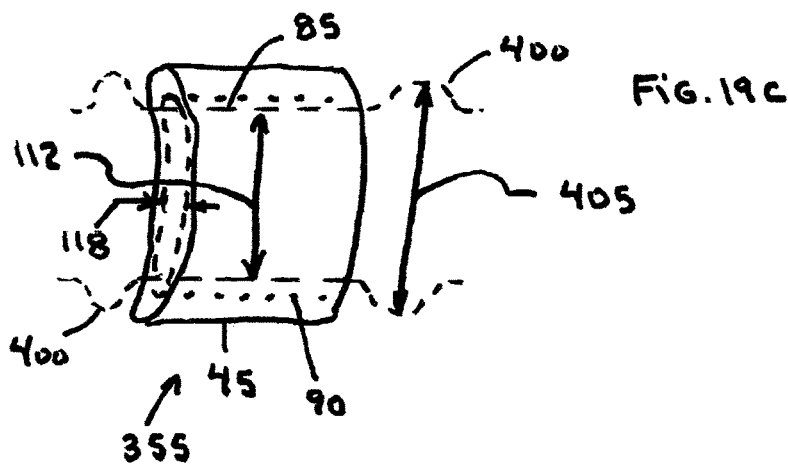
FIG. 19C

PERIVALVULAR OCCLUSION DEVICE AND METHODS

CROSS REFERENCE TO RELATED APPLICATIONS

This patent application makes reference to and thereby incorporates all information found in the provisional patent application numbered 62/283,688 entitled Perivalvular Occlusion Device and Methods, filed 8 Sep. 2015 by William J. Drasler.

BACKGROUND OF THE INVENTION

The implantation of Transcatheter Aortic Valve Replacement (TAVR) devices and Transcatheter Mitral Valve Replacement (TMVR) devices has provided significant opportunity for improved health for those patients that are too sick to undergo surgical valve replacement or those who are of significant age of which the trauma associated with surgical replacement does not merit the potential benefits of surgical replacement over transcatheter valve replacement. Although improvements are continuously being made in the TAVR and MTVR devices and their procedures, the presence of leakage of blood across the transcatheter valve in a retrograde direction has raised clinical concerns including the potential increased mortality due to such perivalvular leakage. Such blood leakage is also found with the use of standard surgical valve in the aortic and mitral positions. Occlusion devices have been used to block perivalvular leaks that occur following the implantation of surgical and transcatheter aortic and mitral valves however the occlusion devices can themselves cause problems to occur. These devices are not optimally designed for blockage of the thin, oval, crescent-shaped opening that occurs in perivalvular leaks. A typical standard occlusion device often will have a circular cross section and is not specifically intended to undergo a shape change during expansion that will fill the voids found in a channel that has an oval or crescent-shaped cross section. Also, the current occlusion devices typically have flanges on either end of the device to prevent such devices from migrating; these flanges tend to interfere with valvular function and with blood flow through the valve. What is needed is an occlusion device that conforms to a thin, crescent-shaped opening, blocks blood flow through such opening, cannot migrate, and does not Interfere with valvular function and blood flow through the valve.

SUMMARY

The present invention is an occlusion device that is intended to block blood flow through a thin, crescent-shaped perivalvular leak path or channel that occurs around a surgically implanted aortic valve or a mitral valve, or around a TAVR or TMVR device. Several embodiments of balloon expandable (BE) systems and self-expanding (SE) systems of the present invention are described. In general the device consists of a stent-like structure that is delivered to the perivalvular leak in a small configuration and is enlarged to fill the thin, crescent-shaped leak path of the perivalvular leak. The stent or stent-like structure contains a covering material attached to the stent and a blocking fabric that extends across the cross section of the stent. The covering and blocking fabric are formed from thin blood resistant material that serves to block blood flow through the stent wall and/or through the stent lumen, and hence block the perivalvular leak that extends through the channel. The blocking fabric can be contiguous with the covering material and can extend over one of the open ends of the stent. The covering can be a polymeric film that is similar to a dilation balloon material and can hold pressure. Alternately, in some embodiments the cover can be a fabric that is formed from a porous material that will eventually become occluded and thereby result in occlusion of the leak channel.

Although most of the discussion found in the present specification is directed toward blockage of a perivalvular leak that occurs around a TAVR device, it is understood that the discussion applies also to leaks that can occur around any implanted valve of the heart including surgically implanted valves and transcatheter devices, and also the device of the present invention can be used to block blood-flow leaks or other fluid leaks found around the outside of any implanted device or in some cases within an implanted device. The present occlusion device is delivered via a percutaneous or transcatheter approach to the vasculature or other vessel of the body.

A perivalvular leak is generally created by the presence of a channel that extends along the outside of a TAVR device or surgically implanted valve (or other implanted device); the channel is often found to have an oval or crescent-shaped cross section; the major axis of the oval extends around a portion of the perimeter of the implanted valve for a distance of several millimeters (range 1-10 mm) in the circumferential direction. The minor axis of the oval channel extends in the radial direction and is generally smaller in dimension (approximate range 0.5 mm to 3 mm), but is large enough such that the blood flow in a retrograde direction across the valve is enough to cause clinical concern to the patient that can influence patient mortality. The axial length of the channel in an axial direction extends along the length of the TAVR device or implanted valve and can range from approximately 3 mm to over 15 mm.

The channel that forms the perivalvular leak has a generally undulating shape throughout the surface of the channel. The cross section is generally not formed as a perfect oval but instead has many undulation protrusions and cavities that can be formed from calcium deposits located along the native valve leaflets. Such undulation also extends along the axial length of the channel. The stent structure of a TAVR device or the sewing ring of a surgical valve can also form undulations in the channel shape that can protrude into the channel or form pockets and cavities that make up the surface of the perivalvular channel. The present invention is intended to extend into and around these cavities and protrusions to form a tight fit into the undulations that will prohibit migration of the occlusion device and will improve the ability of device to block blood flow through the channel.

The present invention is specifically designed to fill an oval channel that is thin (0.5-3 mm) in its minor axis distance (typically in the radial direction for a TAVR device), long (1-10 mm) in its major axis distance (typically extending in the circumferential direction along a portion of a perimeter for a TAVR device), and having an axial length of 3 to more than 15 mm in axial length. The device is delivered to the perivalvular leak site in a small diameter configuration and is expanded out via either a balloon inflation method or via a self-expansion of a stent-like structure or stent to fill the oval void of the channel cross section. The stent is designed to fill in the voids and nonuniform spaces found within the channel such that the occlusion device will not migrate once it is expanded and released into the channel. A covering or blocking fabric that is attached to least a portion of the stent will extend into the blood-flow path of the channel to block blood flow through the channel.

In one embodiment, the occlusion device is a stent with a generally cylindrical shape in its nondeployed small diameter configuration and having a covering attached along a portion or along its entire cylindrical surface. The covering also extends across one end of the stent and forms a closed covering end that will block blood flow after the device has been expanded to a larger diameter within the perivalvular leak channel. The stent and covering can be loaded onto a balloon catheter having an expandable balloon located at its distal end. The balloon catheter can be an over-the-wire catheter such that it is able to follow over a standard guidewire that is initially placed across the perivalvular leak channel. The closed covering is designed with a small flapper valve to allow a guidewire to pass through the covering but upon removal of the guidewire, the closed covering will block blood passage through the occlusion device.

The expandable balloon located at the end of the balloon catheter is formed from an elastomeric material such that it can reduce in diameter back to its original low diameter and cylindrical profile upon deflation. The low profile for the balloon allows it to be removed from the thin oval channel without causing friction against the occlusion device that could cause the implanted occlusion device to migrate during the removal of the balloon catheter following balloon inflation to expand the occlusion device and subsequent deflation of the balloon prior to catheter withdrawal. The balloon can be formed with a generally tapered or conical shape with a smaller balloon diameter at the distal end of the balloon to provide a relief for the balloon upon withdrawal from the narrow or thin oval channel without causing frictional drag that could cause migration of the occlusion device upon removal of the balloon catheter. The balloon can be coated with a lubricious coating to reduce friction with the occlusion device and allow improved removal of the balloon with less frictional force. The balloon can also be formed from a noncompliant or semicompliant material although such balloons will often not refold and could cause friction against the occlusion device.

The stent-like structure or stent for the balloon expandable embodiments can be formed from a plastically deformable metal such as stainless steel, titanium, or other metal or alloy used in coronary and peripheral vascular stenting that can be deformed into the undulations found in the perivalvular channel. The stent can be formed using standard laser cutting technology into a metal tubing of stainless steel or via a wire structure that forms the stent. The stent design can be similar to stent designs used in the coronary or peripheral stent applications. Alternately, the stent design can have a hinge and strut structure that allows for ease of bending at the bending sites or hinges and a larger width for the struts that makes contact with the surface of the balloon such that an elastomeric balloon can push out the stent into the oval shaped channel and push both the hinges and struts into the undulations of the channel without causing excessive local deformation of the balloon. It is anticipated that the stent would deform into the undulations via a low balloon pressure of approximately 1-2 atm. (range 0.5-6 atm.). In a further alternate structure for the stent, the hinges can be enlarged in their radial dimension such that they bend easily during expansion deformation of the stent but the hinges do not bend easily in the radial direction, the struts of this structure are able to extend and bend into the undulations of the channel where the balloon expandable hinges provide the hold the struts into the expanded diameter configuration for the stent.

An additional embodiment for a BE occlusion device provides a balloon located at the end of a catheter shaft that serves both as an inflation balloon and as a closed covering that block blood flow. In this embodiment the balloon has a stent located along a portion or all of the outer surface of the balloon and the distal end of the balloon occlusion device forms a closed covering or blocking fabric located at the distal end. This embodiment is not an over the wire system and hence is delivered to the site of the perivalvular leak channel through an outer sheath. Once the balloon has reached the channel, it is inflated to expand the balloon and stent into the undulations of the channel. The balloon is then detached from the shaft of the catheter via a screw-and-thread-type of attachment or via other attachment and detachment mechanisms. The balloon can be inflated with saline which can be allowed to escape following expansion of the stent into the channel undulations. Alternately, a small duck-bill valve or flapper valve can be located near the proximal end of the balloon in order to retain pressure and retain the fluid contained in the balloon. If a valve is present in the balloon, then a polymer such as a polyurethane or epoxy, for example, can be used to fill the balloon and form a cured polymer with a retained polymer shape within the balloon. Other occlusion systems are described that allow an over-the-wire delivery of a BE occlusion device wherein the balloon is released from the catheter shaft forming both the inflation balloon and the closed covering.

A self-expanding (SE) embodiment for the occlusion device of the present invention includes a SE stent with a covering that covers all or a portion of the stent; the covering is a closed covering or blocking fabric at the distal end, proximal end, or at a location between the proximal and distal end to form blockage for blood flow through the occlusion device. The occlusion device is delivered to the site of the perivalvular leak within an outer sheath that holds the occlusion device in a small diameter configuration. In one embodiment the closed covering or blocking fabric is located at the distal end of the occlusion device and has a guidewire tubing extending through the closed covering. The closed covering has a structure such as a flapper valve or it can be formed from a material that has elastomeric character that allows the covering to close once the occlusion device has been released from the sheath into the perivalvular leak channel and the guidewire tubing has been removed. The SE stent is designed to expand into the undulations found in the oval-shaped perivalvular leak channel.

Another embodiment for the SE occlusion device provides a covering located over all or a portion of a SE stent without the presence of a guidewire tubing. The stent is delivered to the site of the channel within a sheath which holds the SE stent into a small diameter configuration. Upon release from the outer sheath, the SE stent expands into contact with the undulations of the perivalvular leak channel.

The stent structure for the SE occlusion device can be any SE stent structure found in coronary or peripheral medical device use. The material can be an elastomeric metal such as Nitinol (NiTi), Elgiloy, or other elastomeric metal or material including stainless steel and elastic polymers which can behave elastically if deformed locally to small relative deformations in comparison to its thickness.

In one embodiment for the SE stent, the stent is made up of hinges and struts that have a specific geometry; the hinges are formed with a greater thickness in the radial dimension in order to provide a greater outward force in a circumferential direction during expansion deformation. The greater outward force ensures that the stent is fully deployed to a large diameter configuration and extend into the far reaching undulation and extent of the oval or crescent-shaped cross section of the perivalvular leak channel. The struts are formed such that they have a width in the plane of the cylindrically-shaped nondeployed stent that is large in comparison to the width of the hinges; thus the hinges cause the struts to extend outwards to achieve a large diameter for the expanded stent without bending of the struts in a circumferential direction or in the direction of the hinge expansion deformation. The struts are thin in the radial direction in comparison to the radial dimension of the hinges such that the struts can bend easily in the radial direction and fill in the undulations and sharp radii of curvature found in the channel. The struts can be formed from a SE material or can be softened to form a plastically deformable material that can more easily bend into the undulations of the channels. Also, the struts can be formed from an elastic material that is thin in the radial dimension (in comparison to the hinge radial dimension) and can bend easily into the undulations associated with the channel cavities and protrusions.

The struts can also be formed such that they have a crown located along a width of a strut. The crown will allow the strut to bend more easily in a direction toward the concave side, toward the outside of the perivalvular leak channel. Placement of the crown towards the outside surface of the stent will allow the strut to bend more easily into the undulations and fill into the small radii of curvature bends located at the major axis of the oval-shaped cross section of the channel and not collapse toward the inner lumen of the stent. Other embodiments are presented to allow the strut to bend outwards more easily than inwards thereby providing a structure that is held tightly against the surface of the channel without collapsing toward the center of the channel and leaving a channel for blood flow still remaining.

The SE stent structure can have either a cylindrical shape or an indented shape in its nondeployed configuration and expand outwards upon release from the sheath to form a further indented shape that blocks blood flow through the central lumen of the stent. Such a shape can be formed from thermal methods into a NiTi stent structure. Alternately, the stent can be formed with metal struts or stent elements that extend across the lumen of the stent from one side of the stent to the other side approximately 180 degrees around its perimeter. Such stent elements can be used to hold a covering or blocking fabric or serve via itself as a blocking member or blocking fabric to cause blood flow to be occluded either acutely or over a time period of days or weeks and not allow blood flow to occur through the lumen of the stent.

The SE stent can also be formed with the presence of bulbs at each end of the stent; the bulbs representing a region of the stent having a larger equilibrium diameter in its fully expanded configuration. The presence of such bulbs can allow the stent to be positioned with one bulb on each side of the channel to help assist with prevention of migration of the occlusion device within the channel.

In yet another embodiment for the SE occlusion device, the SE covered stent with a closed covering to block flow through the stent or channel can be placed within a sheath for delivery as described earlier with the additional presence of a dilation balloon contained within the lumen of the stent. The balloon, as described earlier, can be an elastomeric balloon that returns to its original shape following expansion within the occlusion device. This embodiment provides an effective postdilation to the SE stented occlusion device and ensures that the occlusion device is well seated within the channel thereby minimizing likelihood for migration of the occlusion device.

In further yet another embodiment for the SE occlusion device, the SE stent can be contained within a balloon or positioned on the outside of a balloon that is filled with either saline or a curable polymer. The balloon can be formed from a noncompliant or semicompliant material that extends easily to cover the perimeter of the channel. The occlusion device is first released from the sheath and allowed to expand outwards into the channel. The balloon is then inflated with saline or polymer to force the balloon and covering into contact with the undulations of the channel and push the stent into intimate contact with all aspects of the channel. Then the balloon is released via a thread and screw mechanism, for example. A valve can be provided to prevent escape of the polymer or saline following expansion of the balloon.

BRIEF DESCRIPTION OF THE DRAWINGS

FIG. 2A is a longitudinal sectional view of an occlusion device in an non-expanded configuration.

FIG. 2B is a cross-sectional view of an occlusion device.

FIG. 2C is a longitudinal sectional view of an occlusion device across its major axis in an expanded configuration.

FIG. 2D is a cross-sectional view of a channel that causes a perivalvular leak.

FIG. 2E is a longitudinal sectional view of an occlusion device across its minor axis in an expanded configuration.

FIG. 3A is a longitudinal section view of an occlusion device mounted onto a dilation balloon in a nondilated configuration and having a guidewire tube extending through a flapper valve.

FIG. 3B is a longitudinal section view of an occlusion device mounted onto a dilation balloon in a nondilated configuration and having a guidewire tube extending directly through the blocking fabric.

FIG. 3C is a longitudinal section view of an occlusion device mounted onto a dilation balloon in a dilated configuration and having a guidewire tube exending through a flapper valve.

FIG. 3D is a perspective view of the occlusion device positioned within a channel.

FIG. 3E is a cross-sectional view of a flapper valve.

FIG. 3F is a longitudinal section view of a tapered balloon in an inflated configuration having an occlusion device mounted on its outer surface.

FIG. 4A is a cross-sectional view of an occlusion device with a blocking fabric that forms a closed distal end mounted onto a noninflated dilation balloon.

FIG. 4B is a cross-sectional view of an occlusion device with a blocking fabric that forms a closed distal end mounted onto an inflated dilation balloon.

FIG. 4C is a perspective view of an occlusion device located within a channel that formed a perivalvular leak.

FIG. 4D is a cross-sectional view of an occlusion device with a blocking fabric that forms a closed distal end mounted onto an inflated dilation balloon that has a central wire extending throughout the length of the balloon.

FIG. 5A is a plan view of a hinges and struts from a ring of the stent wall structure of one embodiment of the occlusion device.

FIG. 5B is a flattened view of a portion of the wall structure of the stent that is found in one embodiment of the occlusion device.

FIG. 7D is a plan view of an occlusion device having a slidable seal located at a distal end of the occlusion balloon for passage of a mandrel or guidewire.

FIG. 9A is a perspective view of the occlusion balloon held onto the delivery tube and released from the delivery tube via a screw mechanism.

FIG. 10A is a longitudinal section view of self-expanding occlusion device held in an nondeployed configuration by an external sheath and having a flapper valve to allow passage of a guidewire tube.

FIG. 10B is a longitudinal section view of self-expanding occlusion device held in an nondeployed configuration by an external sheath and having a guidewire tube extending through the blocking fabric.

FIG. 10C is a cross-sectional view of a flapper valve.

FIG. 10D is a longitudinal section view of self-expanding occlusion device in a deployed configuration and having a flapper valve to allow passage of a guidewire tube.

FIG. 12 is a longitudinal section view of an occlusion device having a stent central region with a narrowing to block the stent lumen.

FIG. 13A is a perspective view of the stent found in the occlusion device showing the stent major axis and stent minor axis.

FIG. 13B is a perspective view of the stent and occlusion device positioned within a channel.

FIG. 14 is a plan view of a stent of the occlusion device showing the wall structure.

FIG. 15A is a perspective view of a hinge and strut wall structure for one embodiment of a self-expanding stent used in the occlusion device.

FIG. 15B is a plan view of a portion of a self-expanding stent wall structure for one embodiment of the occlusion device showing a long hinge length.

FIG. 17A is a longitudinal section view of a stent and covering in a nondeployed configuration.

FIG. 17B is a cross-sectional view of a stent and covering in a nondeployed configuration.

FIG. 17C is a longitudinal section view of a stent in an expanded configuration having a narrowing in the central region of the stent.

FIG. 17D is a cross-sectional view of a stent in an expanded configuration having a narrowing in the central region of the stent.

FIG. 19A is a longitudinal section view of an occlusion device with a self-expanding stent held in a nondeployed configuration by an external sheath.

FIG. 19B is a longitudinal section view of an occlusion device with a self-expanding stent having bulbous ends that has been released from an external sheath.

FIG. 19C is a perspective view of an occlusion device with a bulbous stent that has been implanted in a channel.

DETAILED DESCRIPTION

Figure 1A:
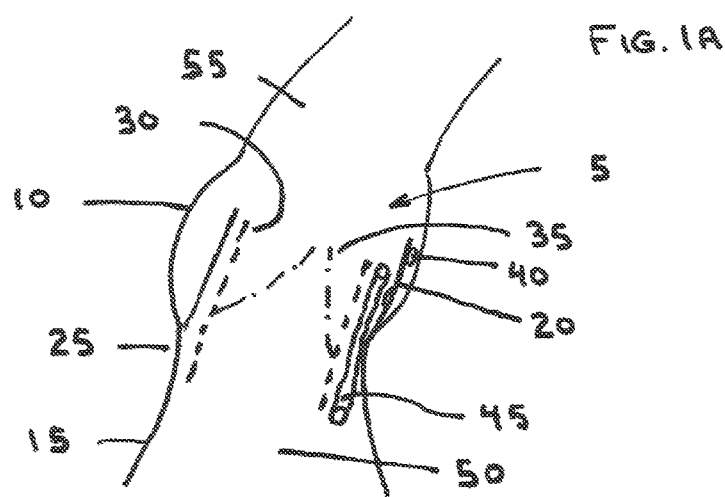
FIG. 1A is a longitudinal sectional view of the aortic root having a TAVR stented device implanted and a longitudinal section of perivalvular leak channel.

FIG. 1A shows the anatomy of the aortic root (5) showing the aortic sinus (10) joined to the left ventricle, LV (15). The native aortic valve leaflets (20) are attached to the annulus (25) and have been pushed to the side via a TAVR stented device (30) that contains TAVR replacement leaflets (35). Calcium nodules (40) located on the back surface of the native leaflets have created a channel (45) that travels between the TAVR stented device and the native leaflets. The channel (45) extends from the aortic sinus past the aortic annulus (25) and into the left ventricular outflow tract, LVOT (50). This channel (45) creates a perivalvular leak that allows retrograde passage of blood from the aorta (55) directly to the LV (15) during diastole.

Figure 1B:
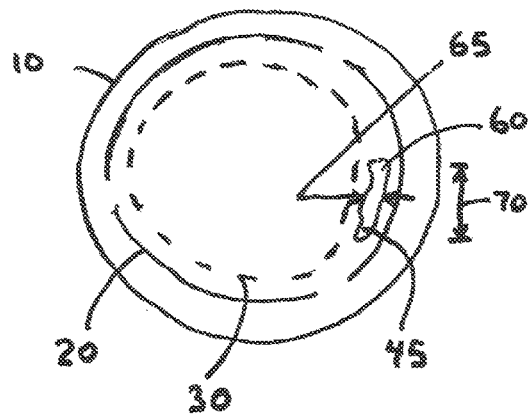
FIG. 1B is a cross-sectional view across the aortic sinus showing a TAVR stented device and a cross-section of the perivalvular channel.
Figure 1C:
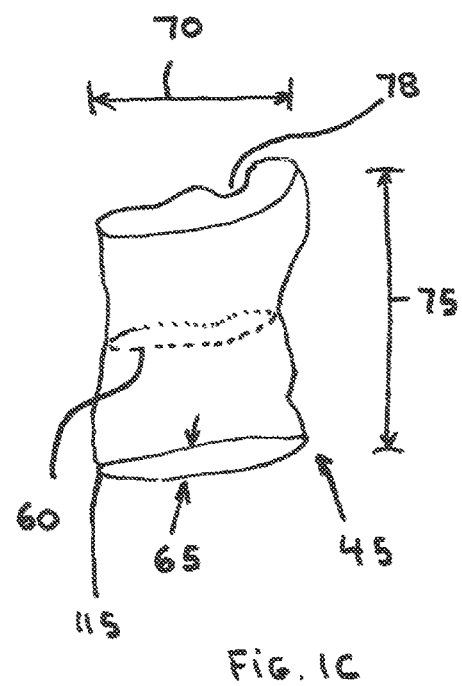
FIG. 1C is a perspective view of a channel that results in a perivalvular leak.

Looking at a cross sectional view of the aortic sinus, as shown in FIG. 1B, one can see that the channel cross-section (60) has an oval or crescent-like shape that extends around a portion of the perimeter of the TAVR device. The channel (45) has a very thin channel minor axis distance (65) ranging from 0.5 mm to up to 3 mm) and a large channel major axis distance (70) ranging from 2 mm to 20 mm. The axial length (75) of the channel (45) as shown in FIG. 1C ranges from 3 mm to over 15 mm. The channel (45) can have numerous undulations (78) formed from the calcium nodules and from the structure of the TAVR stent. The cross section of the channel (45) along the axial length (75) is also highly variable.

FIGS. 2A and 2B show an overview of specific embodiments of the present invention in a nondeployed smaller diameter configuration. The occlusion device (80) has a cylindrically shaped stent-like structure or stent (85) and a covering (90) that is attached to the stent (85) or is in contact with the entire outer surface (95) of the stent (85) or a portion of the stent (85) surface. The covering (90) can be attached to the stent (85) via a variety of methods including thermal bonding, adhesive bonding, encapsulation of the stent (85) within the covering (90) material, suturing, or other methods. The distal end (130) of the covering (90) (or another portion of the covering (90) located at the proximal end of the stent (85) or central regions (355) of the stent) is a closed covering (100) or blocking fabric (100) such that blood in not able to pass through the covering (90) or at least is highly resistive to blood passage and hence blood flow cannot traverse through the lumen (105) of the stent (85) in an expanded configuration. The closed covering (100) or blocking fabric (100) that extends across the stent cross-section (110) can be contiguous with the covering (90) or it can be a separate fabric element that is joined or attached to the stent (85) or covering (90) using selected bonding methods as described for bonding the covering (90) to the stent. The stent (85) can be a balloon expandable stent (85) formed from a plastically deformable metal, polymer, or composite material; alternately the stent (85) can be a self-expanding stent (85) formed from an elastically deformable material that expands outwards to an equilibrium shape that is larger than the smaller diameter delivery configuration upon release from an external delivery sheath. The covering or blocking fabric (100) for embodiments can be a porous fabric such as expanded polytetrafluoroethylene (ePTFE), a fibrous polymer or tissue material, a woven polymer, a solid polymer film such as polyethylene terephthalate, (PET), nylon, polyurethane, Pebax, or other polymer film materials used in medical devices.

In an expanded configuration as shown in FIGS. 2C-2E, the stent (85) has enlarged in diameter to form a stent major axis distance (112) that is the same as the major axis distance of the channel (45). The stent (85) and covering (90) has deformed to fill the undulations (78) formed by the calcium nodules found on the native valve leaflets or from the TAVR stent structure and has extended along the major axis distance (112) to fill the small radius of curvature of the channel bend (115) at the ends of the major axis. The stent (85) and cover extend to form an occlusion device (80) that makes contact with protrusions (120) and cavities (125) found along the perivalvular channel (45); the stent minor axis distance (118) is equal to the channel minor axis distance. This general structure for the occlusion device (80) will be further discussed in subsequent embodiments in more detail.

FIGS. 3A and 3B show an embodiment for a BE occlusion device (80) having a BE stent (85) with a covering (90) positioned along its outer surface (95) and forming a closed covering (100) or blocking fabric (100) at its distal end (130). The BE stent (85) is positioned over a balloon catheter (135) having an expandable balloon (140) located at its distal end (130). A guidewire tube (145) extends through the closed covering (100) to allow passage of the device over a guidewire. The closed covering of FIG. 3B is formed from an elastomeric material such as polyurethane, for example, that closes any opening formed by the guidewire tubing (145) after the balloon has been deflated and withdrawn from the implanted stent. The closed covering can contain a flapper valve (160) as shown in FIG. 3A to provide a closed surface to the closed covering following removal of the inflation balloon. The balloon is formed from an elastomeric material such as polyurethane, silicone, latex, or a composite material that allows return or a majority of return of the expandable balloon (140) to its original diameter following inflation and subsequent deflation of the balloon; alternately, the balloon can be formed from noncompliant or semicompliant materials that are normally used in angioplasty balloons. As shown in FIG. 3C, the balloon is able to reach an inflation diameter (150) that is equal or greater than the channel major axis distance (70). Upon deflation of the balloon, the balloon catheter (135) is withdrawn as shown in FIG. 2D leaving the expanded occlusion device (80) positioned in the channel (45) and making contact with the undulation walls or undulations (78) of the channel (45). A pair of thin silicone or elastomeric flaps (155) can form a flapper valve (160) as shown in FIG. 3E that can be positioned at the distal end (130) of the closed cover or blocking fabric (100) to provide a temporary passage for a guidewire or a guidewire tube (145) that then provides passage for a guidewire; the flapper valve (160) provides for an adequate seal in the closed covering (100) to ensure that blood flow through the occlusion device (80) lumen (105) is blocked. Alternately, fibers having elastic character used in the construction of fibrous elastomeric blocking fabric (100) or closed covering (100) can provide a slidable sealing passageway for the guidewire tubing during delivery of the occlusion device (80) to the channel (45). The balloon of the present invention can be formed with a tapered shape or conical shape forming a tapered balloon (165) with a smaller diameter toward the distal end (130) of the occlusion device (80) as shown in FIG. 3F. Removal of the balloon from the implanted occlusion device (80) will be more easily released and prevent potential migration of the occlusion device (80) in a proximal direction (170) upon removal of the balloon catheter. Other balloons such as noncompliant balloons or semicompliant balloons can also be used to dilate the stent (85) of the occlusion device (80) into contact with the walls of the channel (45); such balloons can form undesirable wings or flattened extensions that can interfere with removal of the balloon catheter (135) if the deflated balloon shape is not adequately controlled.

FIGS. 4A-4D show a BE occlusion device (80) that is not delivered via an over-the-wire (OTW) method of delivery owing to the absence of a guidewire lumen. In this embodiment, the occlusion device (80) is again comprised of a BE stent (85) with a covering (90) attached to either the entire stent (85) or a portion of the stent. The distal end (130) of the covering (90) is a closed covering (100) that does not have any opening for passage of either a guidewire or a guidewire lumen. The occlusion device (80) is positioned onto an expandable balloon (140) located at the distal end of a balloon catheter. To place this balloon across the channel (45), a guidewire is first placed through the channel (45) and then is exchanged for a hollow sheath that allows passage of the occlusion device (80) within its lumen. Following placement of the occlusion device (80) within the channel (45), the balloon is inflated (see FIGS. 4B and 4C) to expand the stent (85) and covering (90) outwards into contact with the walls of the channel (45) and making contact with the undulations (78) of the channel (45). The balloon is then deflated and removed from the occlusion device. The balloon can have a tapered or conical shape as described earlier. The presence of the stent (85) on the outer or inner surface of the covering (90) will provide adequate axial-strength to allow the occlusion device (80) mounted onto an expandable balloon (140) to be pushed across the channel (45) prior to inflation of the balloon. Also, as shown in FIG. 4D, a central wire (175) or support mandrel can be placed, if necessary, from the catheter shaft (180) to the balloon tip to provide additional push-support for pushing the occlusion device (80) across the channel (45).

FIGS. 5A-5B show one embodiment for the stent wall structure (188) for the stent (85) found in a BE embodiment of the present invention. The BE stent (85) has a soft BE hinge (190) that undergoes the bending deformation as the stent (85) is expanded; the hinges are located in the bent regions (195) or hinge regions (195) of the stent structure (188); the hinge (190) deformation allows the stent (85) to be deformed during expansion to a larger diameter as well as being deformed in a radial direction to fill the cavities or form around protrusions that extend into the channel (45). The hinges are joined together by linear elements or struts (200). The material of the stent (85) can be a soft metal including stainless steel, platinum, titanium, and other plastically deformable metals, composites, polymers, and tissue material such as collagen, fibrin, and biodegradable material. The stent structure (188) can be comprised of rings (205) that can have a of a zig zag configuration (208) or zig zag pattern (208), with rings (205) connected via flexible or deformable connectors (210) that provide the stent (85) with axial stability. Other stent structures such as those found in coronary and peripheral vascular stents can also be used to provide the stent (85) or stent-like structure (188) found in the present invention. The struts of the stent (85) can similarly be formed from a plastically deformable material that is able to conform to the undulation within the channel (45). Conformation of the stent (85) to the undulation will provide the occlusion device (80) with the characteristics of avoiding migration of the device out of the channel (45) and also making a tighter seal with the walls of the channel (45) to create an improved blockage for blood flow. The stent structure (188) is generally weaker in some aspects than a stent structure (188) used to support a blood vessel during vascular stenting. The struts and hinges of the BE stent (85) of the present embodiment are thinner (less than 0.003 inch thickness) in the radial dimension (than a vascular stent) in order to allow them to bend more easily into the undulations (78) of the channel (45) under a lower balloon pressure of approximately 1-2 atm. (range 0.5-6 atm.); this lower pressure can be effectively applied by an elastomeric balloon of the present invention; an elastomeric balloon (i.e., formed from silicone, polyurethane, or other elastomeric polymer or composite) is unable to provide the large pressure dilations required by standard angioplasty and vascular stenting balloons.

Figure 6A:
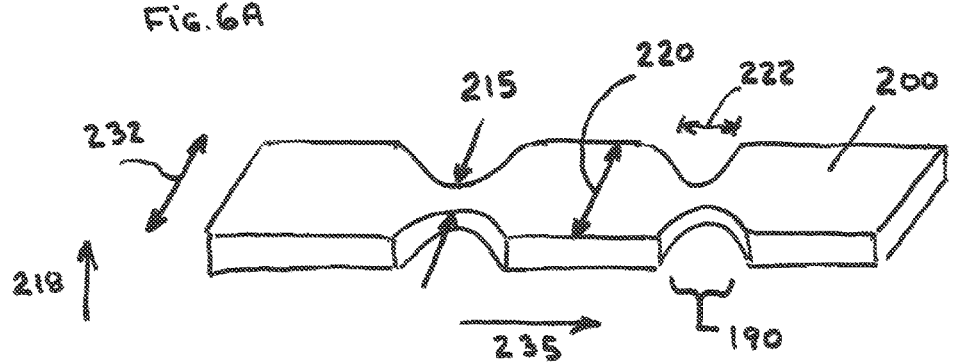
FIG. 6A is a perspective view of a hinge an strut wall structure of a balloon expandable stent having a short hinge length and small hinge radial dimension.
Figure 6B:
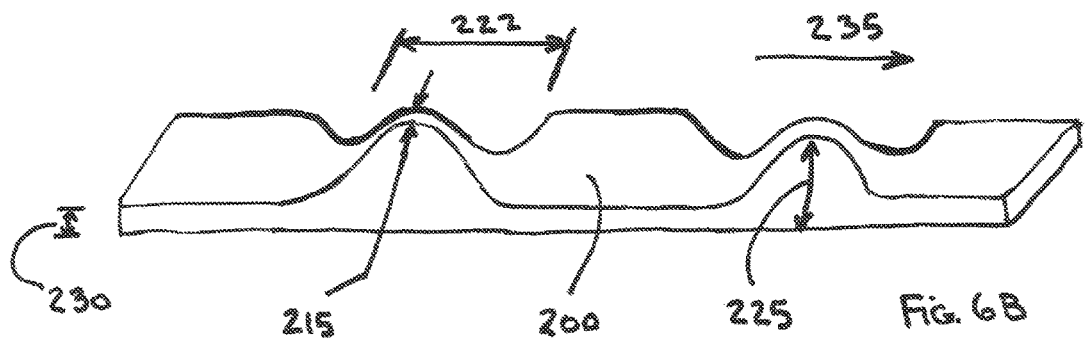
FIG. 6B is a perspective view of a hinge an strut wall structure of a balloon expandable stent having a short hinge length and large hinge radial dimension.
Figure 6C:
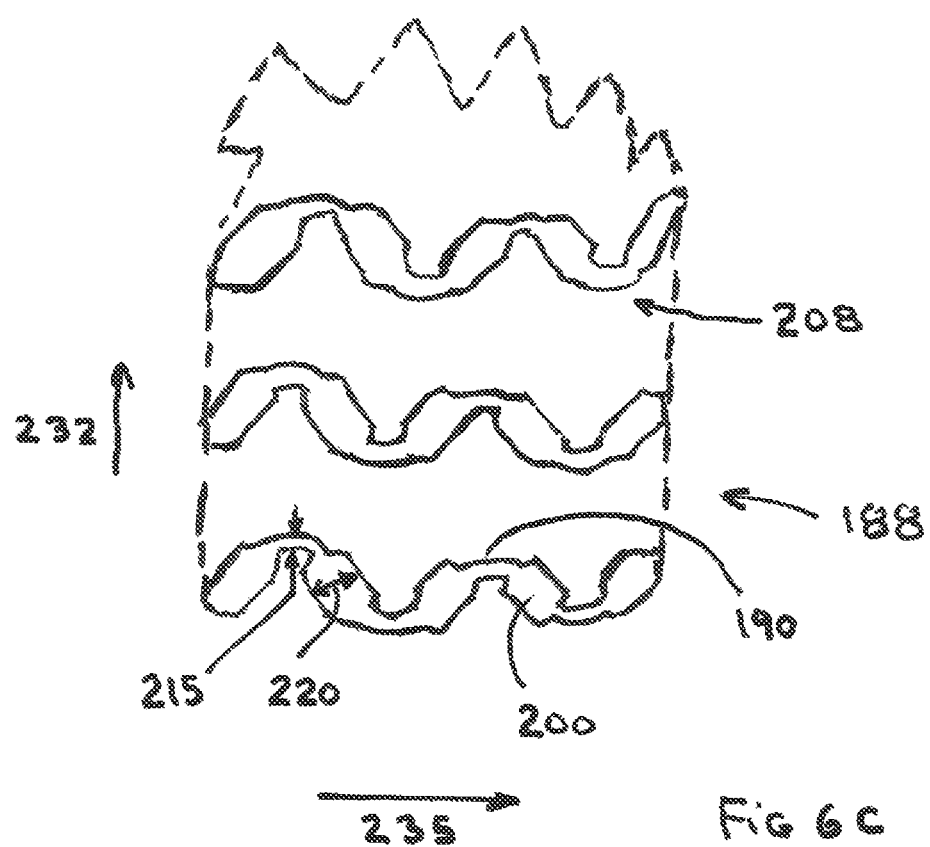
FIG. 6C is a perspective view of a stent having the hinge and stent wall structure of a balloon expandable stent.

Another embodiment for the BE stent (85) of the present invention is found in FIGS. 6A and 6B. In this embodiment for the BE stent (85) the hinge regions (195) are formed such that they are smaller in hinge width (215) than the strut width (220). The stent structure (188) can be formed into a zig zag pattern as shown in FIG. 6C or into any other stent structural pattern used in vascular stents found in the medical device industry. Upon dilating the stent (85) with an expandable balloon (140) such as an elastic balloon, the soft narrow hinges are able to easily deform into the undulations (78) found in the channel (45) both in a circumferential expansion direction as well as a radial direction (218) outwards into channel (45) undulations (78) and around protrusions formed from calcium deposits at generally low pressures of approximately 1-2 atm. The wide strut width (220) allows the elastic balloon to push against the struts to push the struts outwards without significant local deformation of the balloon. The hinge length (222) is short in comparison to the hinge radial dimension (225) so that the expansion deformation will result in plastic deformation of the balloon expandable hinges.

A further embodiment for the BE stent (85) of the present invention is shown in FIGS. 6B and 6C which has hinges having a larger hinge radial dimension (225) extending in the radial direction (218) than the strut radial dimension (230). Several rings (205) of zig zag pattern can be positioned adjacent to each other in an axial direction (232) to form a stent structure (188). During expansion deformation in the circumferential direction (235), the hinges (190) deform plastically but the larger strut widths which are larger than the hinge width (215) are unable to bend in the circumferential direction (235) or the direction of hinge expansion and hence the struts are forced outwards to a larger diameter during balloon expansion; the large strut widths also provide larger area for the elastic balloon to push against without causing local balloon deformation of an elastomeric balloon. The thin strut radial dimension which are thinner than the hinge radial dimension (225) allow the struts to bend into the undulations (78) and make small radius of curvature bends located at the ends of the major axis of the channel (45). Thus expansion of this stent structure (188) (see FIGS. 6B to 6C) allows improved apposition of the stent (85) and the covering (90) attached to the outer surface (95) of the stent structure (188) with the undulations (78) in the channel (45).

The struts (200) of the stent (85) can be formed from with elastic character even if the hinges are formed from material with plastically deformable character. The struts (200) can be formed from an elastic material such as Nitinol (NiTi), for example, or alternately can be formed with a very thin radial dimension (i.e., less than 0.003 inches) out of a stainless steel, cobolt chrome, or other metal or alloy that would normally behave in a plastically deformable manner. The hinges (190) can be formed from the same material as the struts and perform with a balloon expandable or plastically deformable character. Hinges (190) that are formed from stainless steel, cobalt chrome, or other plastically deformable material will perform in a balloon expandable manner. Alternately, the use of Nitinol or other elastic material normally used in self-expanding stents can be used for the hinges (190) so long as the hinge length (222) is short in comparison to the hinge radial dimension (225) thereby causing the hinge to become plastically deformed during the expansion deformation of the stent (80). The Nitinol or elastically deformable material used in the stent can also be thermally treated locally to cause the hinge to become platically deformable and the struts (200) to remain elastically deformable.

Figure 7A:
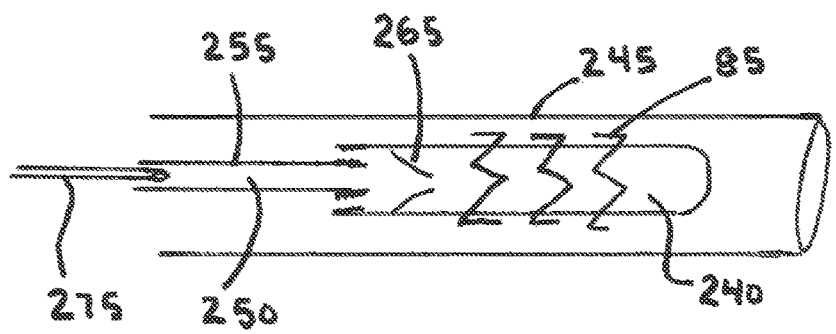
FIG. 7A is a plan view of a balloon expandable occlusion device in an nondeployed configuration delivered by an external sheath.
Figure 7B:
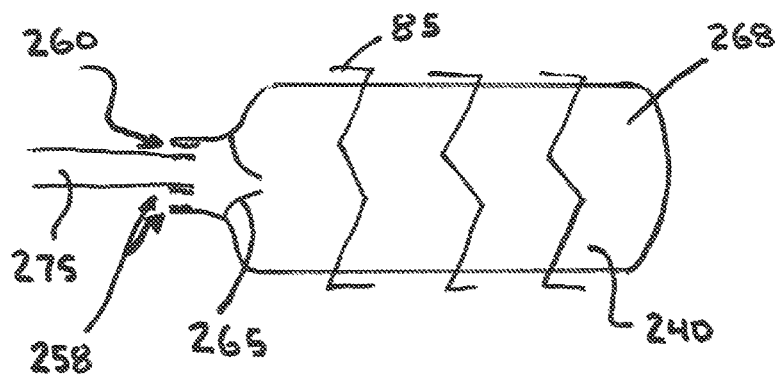
FIG. 7B is a plan view of a balloon expandable occlusion device inflated to an inflated volume with inflation medium that is delivered from the delivery tube.
Figure 7C:
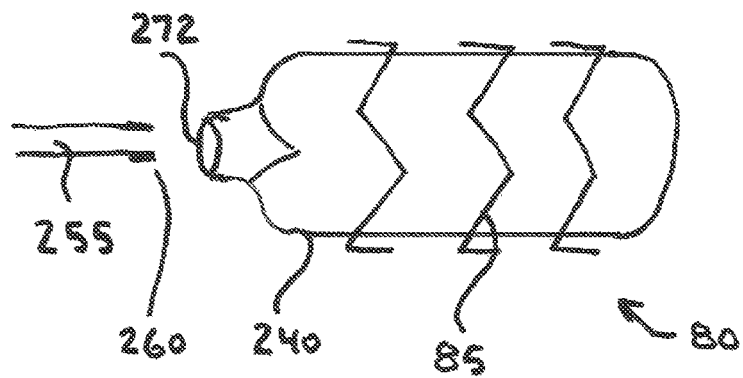
FIG. 7C is a plan view of a balloon expandable occlusion device inflated with inflation medium and released from the delivery tube.

Yet another embodiment for the BE occlusion device (80) of the present invention is shown in FIGS. 7A-7C. In this embodiment an occlusion balloon (240) that is used to inflate the stent (85) serves additionally as the covering (90) and blocking fabric (100). The occlusion balloon (240) serves as a blocking fabric (100) that prevents blood flow through the lumen (105) of the stent (85) and through the channel (45). The occlusion balloon (240) which serves as the covering (90) and blocking member for this embodiment is formed from an elastic material such as silicone or polyurethane, for example, can be used to form the occlusion balloon (240) and also serve as the covering (90) material and blocking fabric (100). The elastic material for the occlusion balloon has an areal strain capability of at least 200% (range 200-500%) in order to push the stent outwards during balloon inflation into the undulations found in the channel.

Alternately, a noncompliant or minimally compliant balloon material (i.e., less than 5% difference in diameter over the pressure range of the balloon during Inflation) such as PET, some low compliance nylons, and other polymer materials used in low or non-compliant balloons can be used. Such noncompliant balloons will require unfolding as they are inflated into the narrow channel; a lubricious balloon material such as polyethylene, Nylon, Pebax, and other materials can provide this unfolding characteristic. Other occlusion balloon materials that undergo some plastic deformation that is retained such as some plastically deformable Pebax films and polyolefin films can also be used to form the occlusion balloon (240) which also serves as the and covering (90) material. The BE stent (85) can be attached to the balloon on the outside or inside surface of the balloon or it can be placed into contact with the outside surface of the balloon. In this embodiment the balloon and stent (85) are placed across the channel (45) through an external sheath (245). After removal of the sheath, the balloon is inflated via an inflation lumen (250) of a delivery tube (255) with either saline or a curable polymer such as a polyurethane, epoxy, or other curable polymer material as shown in FIG. 7B. The occlusion balloon (240) is held to the delivery tube (255) via the holding assembly (258) thereby allowing the occlusion balloon to be filled with inflation fluid via the delivery tube. After delivery of the inflation medium, the balloon is detached from the shaft of the delivery tube (255) via a holding assembly (258) such as a screw and thread mechanism (260), for example, as shown in FIG. 7C or other attachment and detachment mechanism. One element such as a threaded surface, for example, of a thread and screw holding assembly (258) is located on the occlusion balloon and the other element is located on the delivery tube (255). A duckbill valve or check valve (265) located at the proximal end (270) of the occlusion balloon (240) can be used to prevent backflow of polymer or saline out of the balloon following delivery of the occlusion device.

For the case that saline alone is used to inflate the balloon, the check valve for an embodiment can be omitted and the saline inflation fluid or dilute contrast medium inflation fluid allowed to drain out of an open orifice (272) of the occlusion balloon (240) following inflation of the occlusion balloon and detachment of the delivery catheter (255) from the occlusion balloon (240). The inflation volume of inflation medium used to inflate the occlusion balloon to its inflated volume (268) as shown in FIG. 7B can freely flow out of the occlusion balloon (240) through the open orifice (272). The advantages associated with using saline or saline-based inflation fluid (rather than a curable liquid to solid polymeric material) are: a lower occlusion balloon (240) profile due to omission of the check valve, and ease of use due to allowance for leakage of saline (as opposed to a major concern for leakage of a liquid polymer) into the blood stream during balloon inflation and following balloon detachment. A hollow mandrel or hollow tube (275) can be placed within the inflation lumen of the delivery tube (255) and across the check valve, if necessary, to drain the saline inflation mediuiiu out of the balloon in the presence of the check valve (265).

As shown in FIG. 7D the occlusion balloon (240) can be formed such that a slidable seal (325) is located in the distal end of the occlusion balloon (240). The slidable seal allows passage of a guidewire (330) or a mandrel through the slidable seal such that inflation fluid cannot pass between the slidable seal and the guidewire during inflation of the occlusion balloon (240). When saline or saline-base contrast medium is used to inflate the occlusion balloon, leakage of inflation fluid is tolerated past the seal and into the blood stream during balloon inflation. The stent (85) can still be properly deployed even though the slidable seal does not provide a perfect seal without leakage of inflation fluid. If a curable polymer is used to inflate the occlusion balloon, the slidable seal cannot allow leakage of the polymeric inflation fluid. The slidable seal provides the occlusion device with the capability of being delivered to the site within the channel over a guidewire.

Figure 8A:
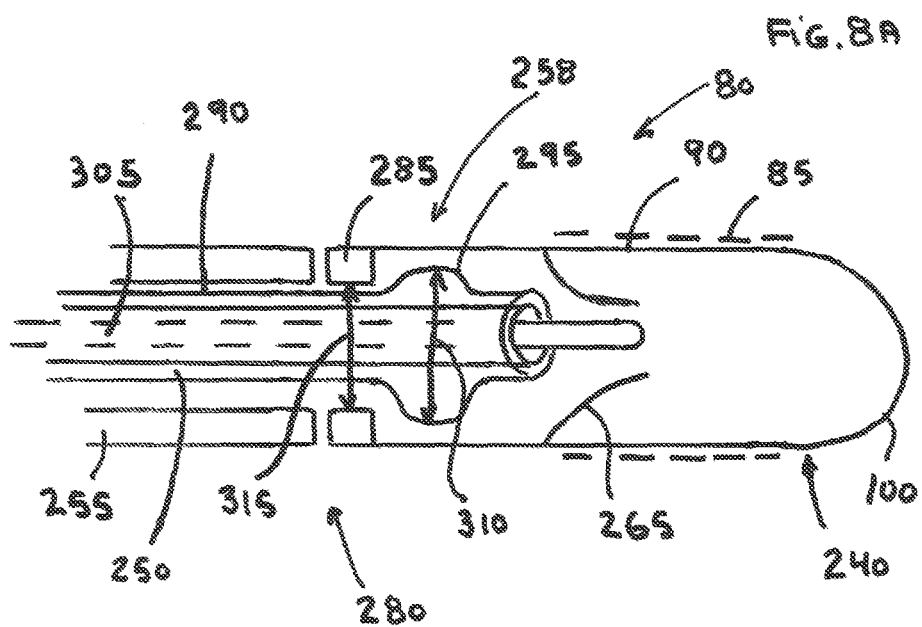
FIG. 8A is a balloon expandable occlusion device that is held during inflation via a delivery catheter having a mandrel.
Figure 8B:
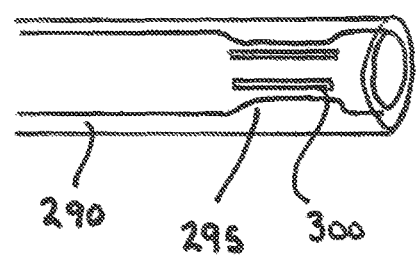
FIG. 8B is a perspective view of a hollow member used to hold the occlusion balloon relative to the delivery catheter during inflation of the occlusion balloon.
Figure 8C:
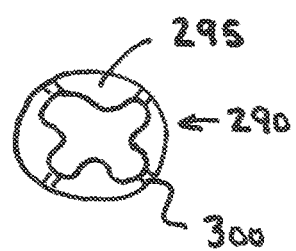
FIG. 8C is a cross-sectional view of the hollow member showing the member stop and slits.

FIGS. 8A-8F show another holding assembly (258) to allow both attachment for filling and provide detachment of a BE occlusion device (80) from the delivery tube (255) wherein the occlusion balloon (240) is serving also as the covering (90) and blocking fabric (100) for the occlusion device. The occlusion balloon (240) which is detachable from the delivery tube (255) is located at the distal end (280) of the delivery tube (255). The occlusion balloon (240) is formed from a material similar to that described in the embodiment of FIGS. 7A-7C. The occlusion balloon (240) has a balloon stop (285) or narrowed diameter region at its proximal end (270) which serves as one element of the holding assembly (258). Another element of the holding assembly (258) comprises a hollow member (290) that has four member stops (295) that extend through the delivery catheter or delivery tube (255) and across the balloon stop. The hollow member has four slits (300) that are located in an axial direction (232) between each of the member stops (295) as shown in FIGS. 8B and 8C.

Figure 8D:
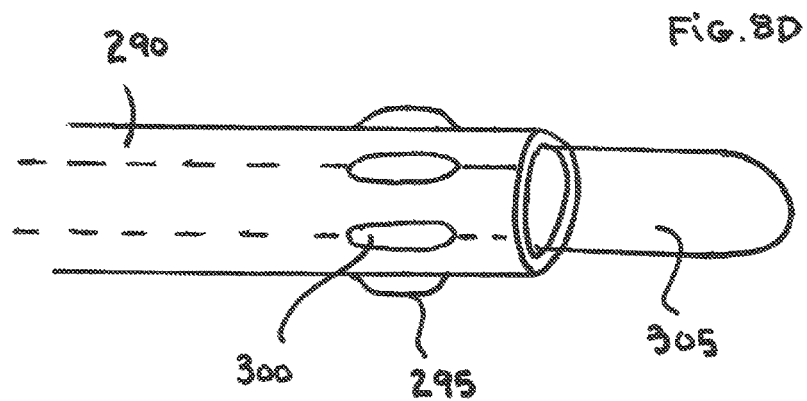
FIG. 8D is a perspective view of the hollow member that holds the occlusion balloon against the delivery catheter and also releases the occlusion balloon.
Figure 8E:
FIG. 8E is a cross-sectional view of the mandrel.

Insertion of a mandrel (305) within the hollow member causes the member stops (295) to extend outwards to form a member stop diameter (310) that is larger than the balloon stop diameter (315) as shown in FIGS. 8D and 8E. Gentle tension placed on the hollow member will hold the occlusion balloon (240) into contact with the delivery tube (255) as long as the mandrel (305) is contained within the hollow member. Inflation of the occlusion balloon (240) can then occur via the hollow member when the occlusion balloon (240) is positioned within the channel (45). Inflation medium can enter the balloon via spacing between the hollow member and the mandrel (305). Inflation of the occlusion balloon (240) causes the stent (85) and the occlusion balloon (240) to come into intimate contact with the channel (45) wall and filling in the undulations (78) in the channel (45). After the balloon has been inflated with either saline or polymer the mandrel (305) can be withdrawn thereby allowing the member stop diameter (310) to become smaller than the balloon stop diameter (315). The hollow member can then be withdrawn leaving the inflated balloon contained within the channel (45). A duckbill valve or check valve can be used to prevent the polymer or saline solution from exiting the proximal end (270) of the balloon.

Figure 8F:
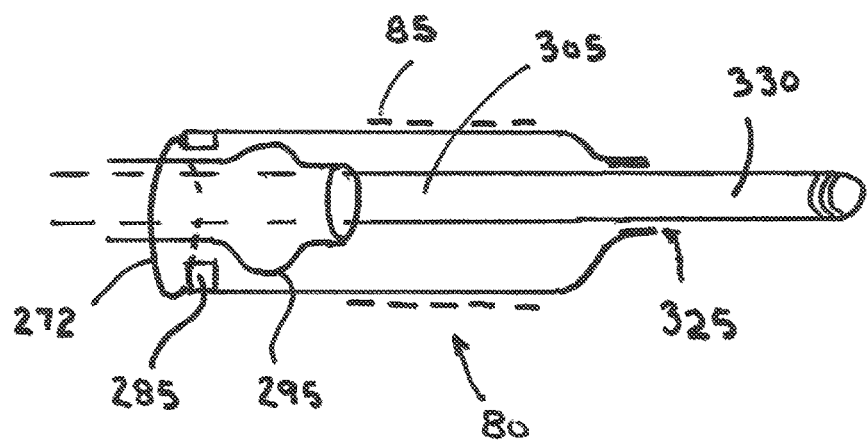
FIG. 8F is a longitudinal sectional view of an occlusion device having a guidewire passing through a slidable seal.

The check valve can be omitted if saline or dilute contrast is used to inflate the occlusion balloon; the saline being allowed to freely flow out of the occlusion balloon (240) after implant; for this embodiment the occlusion balloon proximal end (270) has an open orifice (272) that allows free flow of saline or saline-based inflation medium from the inside of occlusion balloon to flow out of the occlusion balloon when detached from the delivery tube (255). All of the inflation fluid volume used to inflate the occlusion balloon to its fully expanded dimensions within the channel is free to flow out of the occlusion balloon through the open orifice (272) when the occlusion balloon is detached from the delivery tube (255). Use of saline inflation medium without a check valve provides advantages of a lower profile occlusion balloon due to omission of the check valve and allow leakage of saline both during inflation of the balloon and after detachment of the balloon without negative consequences to the patient. This embodiment can be delivered to the channel (45) via an external sheath as described for the previous embodiment. Alternately, the occlusion balloon (240) can be modified as shown in FIG. 8F such that a guidewire serves to guide the occlusion device (80) across the channel (45) as well as serve as the mandrel (305). A sliding seal can be located on the blocking fabric (100) to allow passage of the guidewire (330) while blocking flow of inflation medium out of the sliding seal during inflation of the occlusion balloon (240). The occlusion balloon is shown in FIG. 8F without the check valve such that the inflation fluid such as saline, for example, can freely flow out of the open orifice (272) into the blood stream following detachment of the occlusion balloon (240) from the delivery tube (255).

A further embodiment of a BE occlusion device (80) is shown in FIG. 9A. This embodiment provides an OTW BE occlusion device (80) wherein the occlusion balloon (240) serves as the covering (90) and the blocking fabric (100), and the occlusion balloon (240) is detachable from the delivery tube (255) or delivery catheter. The occlusion balloon (240) has a hollow guidewire shaft (320) that provides passage for the guidewire (330) therethrough. The guidewire tubing or guidewire shaft (320) of this embodiment forms a slidable seal (325) with a guidewire (330) at the distal end (130) of the occlusion balloon. The slidable seal (325) is a narrowed region of the guidewire shaft (320) or flapper valve or other sealing mechanism that prevents significant leakage or completely blocks leakage of inflation medium between the guidewire (330) and the guidewire shaft (320) when the occlusion balloon (240) is being inflated. The slidable seal (325) can be designed to allow, for example, up to 50 ml of saline-based inflation fluid to leak through the slidable seal (325) during a single inflation of the occlusion balloon and be well tolerated by the patient. If saline inflation medium is used to inflate the balloon (rather than a contrast medium) of this embodiment, a greater amount of leakage of saline can be tolerated around the slidable seal (325) during balloon inflation. The saline inflation medium enters the balloon through an inflation hole (335) found in the guidewire shaft (320). The saline inflation medium causes the occlusion balloon (240) and the stent (85) to expand into contact with the channel (45) making intimate contact with the undulations. Following inflation, the balloon is detached from the delivery tube (255) via a thread and screw mechanism or other holding assembly (258). The mechanism or attachment and detachment of the balloon can alternately be similar to the hollow tube and mandrel (305) mechanism described in the embodiment of FIGS. 8A-8E.

FIGS. 10A-10D show an embodiment of a SE occlusion device (80) of the present invention. The SE stent (85) has a covering (90) attached to its outer or inner surface. The covering (90) extends around the distal end (130) of the occlusion device (80) forming a closed cover or blocking fabric (100) that prevents blood flow from flowing through the central lumen (105) of the occlusion device. A flapper valve (160) as shown in FIG. 10C can be located at the distal end (130) of the closed covering (100) or blocking fabric (100) to allow temporary passage of a guidewire shaft (320) through the closed cover during delivery of the occlusion device (80) across the channel (45). The SE stent (85) is held via an outer or external sheath (245) into a small diameter configuration during delivery of the occlusion device (80) across the channel (45). A pusher member (345) is located within the outer sheath proximal to the occlusion device (80) to allow extraction of the sheath while maintaining positioning of the occlusion device (80) within the channel (45). Removal of the sheath allows the SE stent (85) and its attached cover to expand outwards into the channel (45) and into the undulations (78) of the channel (45). The guidewire shaft (320) along with the guidewire (330) can be removed either prior to or following release of the occlusion device (80) within the channel (45). The stent (85) is designed to extend to a stent diameter or stent major axis distance (112) that is at least equivalent to the channel major axis distance (65) as shown in FIG. 10D.

The self-expanding stent wall structure (188) is formed from an elastic metal such as Nitinol, Elgiloy, or other metal with elastic or memory character. The configuration for the stent wall structure (188) can have similar zig zag pattern (208) and can contain hinge (190) and strut (200) configurations similar to those described for the balloon expandable wall structure (188). The hinge length (222) for the self-expanding stent wall structure (188) is longer than the hinge width (215) to provide the self-expanding hinge (190) with elastic bending without exceeding an elastic limit during expansion deformation.

Figure 11A:
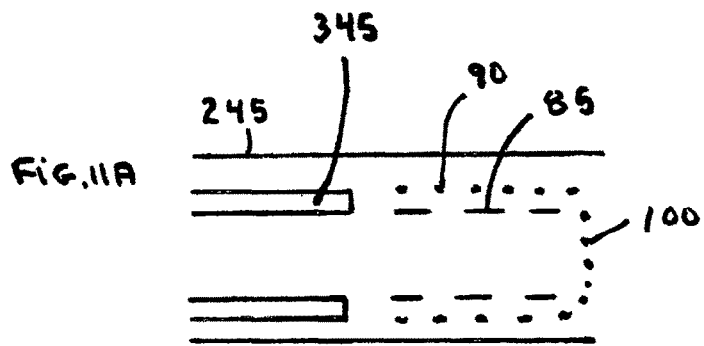
FIG. 11A is a longitudinal section view of a self-expanding occlusion device having blocking fabric over its distal end and held in a nondeployed configuration.
Figure 11B:
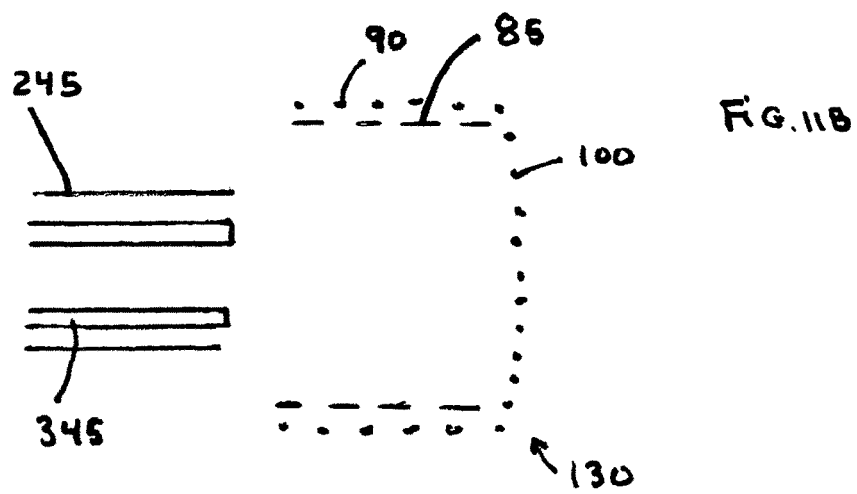
FIG. 11B is a longitudinal section view of a self-expanding occlusion device having blocking fabric over its distal end and released into a deployed configuration.
Figure 11C:
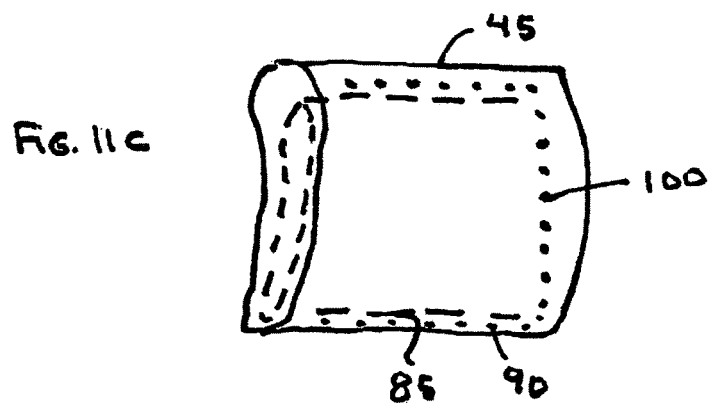
FIG. 11C is a perspective view of the self-expanding occlusion device located in a channel.

An alternate embodiment of the self-expanding (SE) occlusion device (80) is shown in FIGS. 11A-11C. In this embodiment the occlusion device (80) is not delivered over a guidewire (330) but instead is delivered through an external sheath. The SE stent (85) has a covering (90) that extends along the entire stent surface or a portion of the stent inner or outer surface (95) and forms a closed covering (100) or blocking fabric (100) at the distal end (130) as shown in FIGS. 11A and 11B. The blocking fabric (100) can alternately be located at the proximal end (270) or in the central regions (355) of the stent. In a manner similar to that described in the embodiment of FIGS. 10A-10D the SE occlusion device (80) is delivered to the channel (45) via a release from an external sheath and allowed to expand into contact with the channel (45) as shown in FIG. 11C. The stent wall structure (188) allows the stent (85) to easily bend into the undulations (78) of the channel (45) and make intimate contact with the channel (45) wall and thereby both prevent blood flow but also reduce the likelihood for migration of the occlusion device.

As shown in FIG. 12, the SE stent (85) can be formed into a shape that has a narrowing located somewhere in the stent central region (355) between the proximal end (270) and distal end (130) of the stent, or alternately, the narrowing of the stent (85) can be located at the proximal end (270) or distal end (130) of the stent. Upon release from the external sheath as shown in FIG. 12, the stent (85) expands outwards in some regions and remains at a smaller diameter configuration in other regions to ensure blockage of blood flow through the lumen (105) of the occlusion device (80) and hence through the channel (45). The covering (90) not only serves to prevent blood from flowing through the interstices of the stent wall structure (188), the covering (90) also serves as a blocking fabric (100) to block blood flow through the cross section of the stent lumen (105).

The wall structure (188) of the SE stent (85) of the SE occlusion device (80) of the present invention is such that the stent major axis distance (112) should expand outwards to meet the full dimension of the channel major axis distance (65) as shown in FIGS. 13A and 13B even though a neighboring portion of the stent (85) such as the stent minor axis distance (118) is being held at a smaller diameter that is equal to the channel minor axis distance (65).

The SE stent (85) of the SE occlusion device (80) can be formed from SE hinges and SE struts using a stent structure (188) that is similar to other SE stents used for coronary and peripheral vascular stenting. One embodiment for the stent structure (188) provides a zig zag wall structure for the stent (85) with rings (205) formed from an elastomeric metal such as Nitinol (NiTi), Elgiloy, other elastomeric forms of stainless steel, composites, or elastomeric polymers as shown in FIG. 14; other stent wall structures found in vascular stents can also be used for the SE stent of the present invention. The individual zig zag rings (205) can be connected together in an axial direction (232) via connectors (210). The elastic outward force in the radial direction (218) provided by the hinges must be great enough to cause the struts to bend to a small radius of curvature in the radial direction (218) and deform into the undulations (78) in the channel (45).

Another embodiment for the SE stent structure (188) for the SE occlusion device (80) is shown in FIGS. 15A and 15B. In this embodiment the SE stent structure is formed having SE hinges that have a larger hinge radial dimension (225) than the strut radial dimension (230). The hinge radial dimension (225) must be much greater than the strut radial dimension (230) to generate the large elastic expansion force; the strut radial dimension (230) must be thinner (dimension is less than 0.003 inches) than even a normal vascular stent in order to deform to a very small radius of curvature as found at the ends of the major axis of the channel (45). This large hinge radial dimension (225) is intended to provide a larger radial outward force to expand the stent (85) into the undulations (78) of the channel (45) and reach to a stent major axis distance (112) that is equal to the channel major axis distance. The struts have a large strut width (220) that causes them to not bend in the in the direction that the hinges are bending as the hinges open during expansion deformation (circumferential direction). The struts have a very thin strut radial dimension (230) that allows them to bend in the radial direction and bend into the small radius of curvature bends located at each end of the channel major axis. The hinge length (222) is long in comparison to the hinge width (215) such that the hinge (190) does not undergo plastic deformation during expansion deformation and retains its self-expanding elastic character.

Figure 16A:
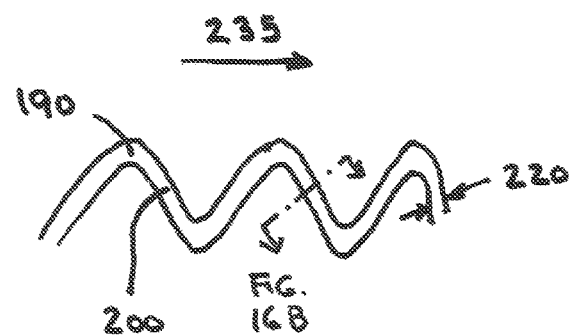
FIG. 16A is a plan view of a zig zag wall structure from a portion of the stent for one embodiment of the occlusion device.
Figure 16B:
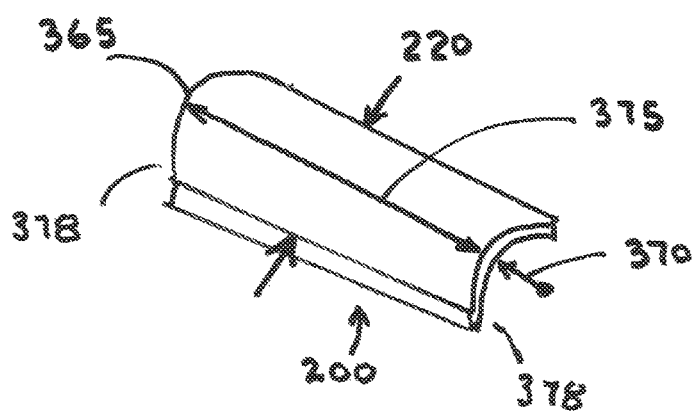
FIG. 16B is a perspective view that shows a stent strut that has a crown in the direction of the stent width.

As the struts are forced to open up during expansion deformation, it is important that they bend with a curvature that favors bending into the small radius of curvature bends located at each end of the major axis of the channel and not bend inwards via a buckling or collapsing mechanism into the lumen (105) of the stent. The stent struts for either the self-expanding or balloon expandable stent wall structures can be formed with a crown in the direction of the strut width (220) and having a strut width radius of curvature (370) along the strut width (220) as shown in FIGS. 16A-16C. This strut (200) will preferentially bend outwards along the strut length (375) from one strut end (378) to the other strut end (378) to fill the cavities and undulations (78) found in the channel (45) and will bend easily to a strut length radius of curvature (380) around a small radius of curvature channel bend (115) located at the ends of the major axis of the channel (45).

Figure 16D:
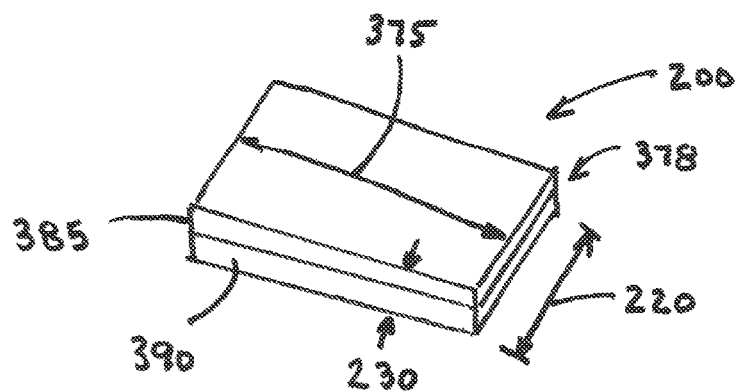
FIG. 16D is a perspective view of a stent strut that has two layers of material forming its strut thickness or radial dimension.
Figure 16C:
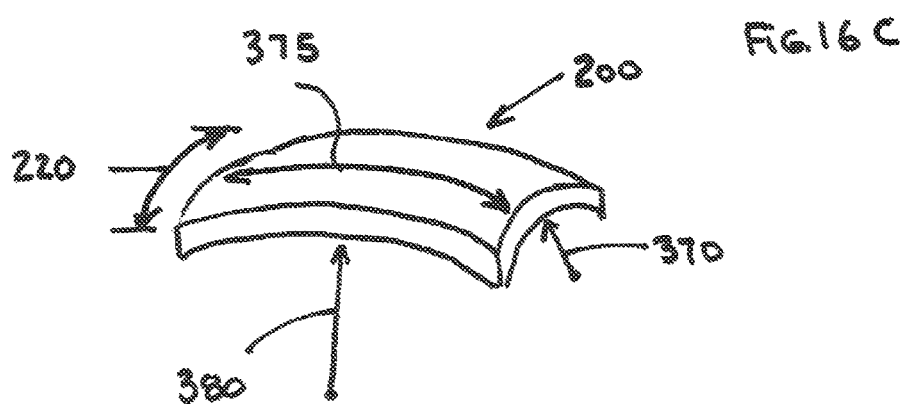
FIG. 16C is a perspective view of a stent strut that has a crown in the direction of the stent width and a crown in the direction of the stent length.
Figure 16E:
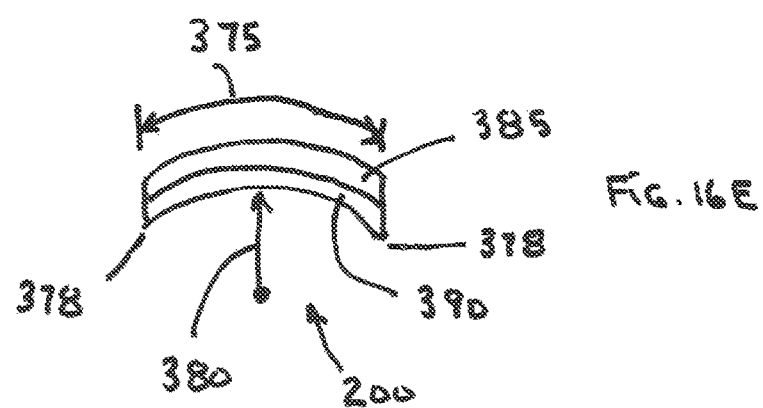
FIG. 16E is a plan view of a strut formed from two materials in the radial direction and bending along the strut length.

An alternate design for a strut (200) is shown in FIGS. 16D and 16E; in this embodiment for the SE strut (200) two different metals or materials are used for forming two layers for the strut. The top layer is formed from a softened metal having a low modulus and the lower layer is formed from a metal with a high modulus. The strut (200) is then able to more easily bend to form a small strut length radius of curvature (380) bend to fill in the small radius of curvature bend located along the strut length (375) or strut width. The soft top layer is better able to stretch than the hard bottom layer; neither layer is able to provide significant compressive strain.

The SE stent (85) of the SE occlusion device (80) can be formed such that it is cylindrical cross-sectional shape in its small diameter configuration (see FIGS. 17A and 17B) and expands out to form a shape that has an equilibrium shape that has a occluding portion (395) of the stent (85) extending into the lumen (105) region of the stent (85) (see FIGS. 17C and 17D). The presence of a covering (90) on the stent (85) surface will then act as a blocking fabric (100) to prevent blood flow through the stent lumen (105) and block blood flow through the channel (45) as shown in FIGS. 17C and 17D. Such an occlusion device (80) embodiment can be delivered by release from an external sheath as described earlier. Alternately, the SE occlusion device (80) can have a non-cylindrical cross-section (110) in either or both its non-deployed or its deployed configuration.

Figure 18C:
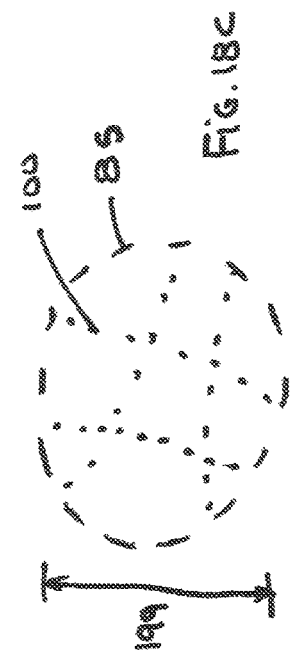
FIG. 18C is a cross-sectional view through the blocking fabric of a stent and covering in a deployed configuration.
Figure 18D:
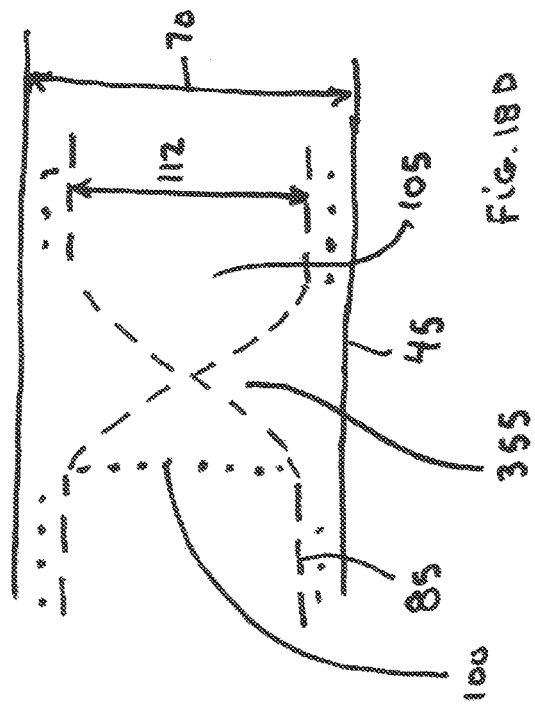
FIG. 18D is a longitudinal section view of a stent and covering with a narrowing of the stent in the central region.
Figure 18A:
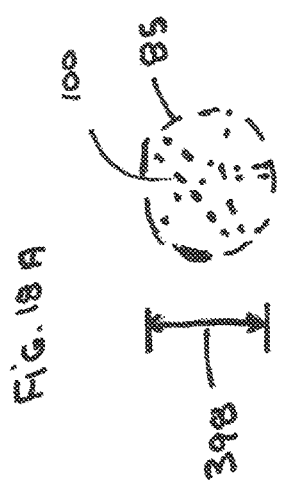
FIG. 18A is a cross-sectional view through the blocking fabric of a stent and covering in a nondeployed configuration.
Figure 18B:
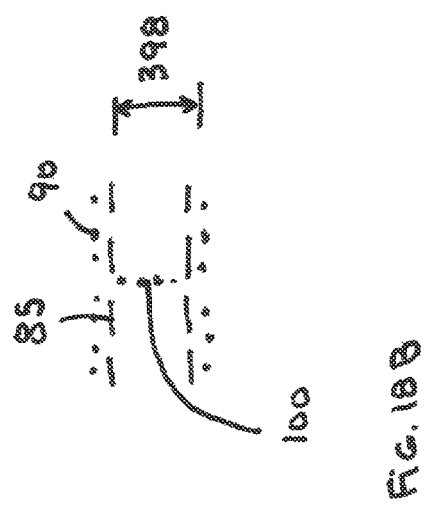
FIG. 18B is a longitudinal section view of a stent and covering in a nonexpanded configuration.

FIGS. 18A-18D show an embodiment for a SE occlusion device (80) that has a SE stent wall structure (188) as described in earlier embodiments. In addition to having a covering (90) that extends along the entire or a portion of the stent structure (188), the stent (85) also contains an internal fabric or blocking fabric (100) that extends across the cross section of one portion of the stent (85) such as a central region (355) (see FIGS. 18A and 18B). The blocking fabric (100) can be a solid polymeric material such as PET, nylon, Pebax, polyurethane, or it can be a microporous material such as ePTFE or polyurethane, or a tightly woven film of polymer or metal or composite fibers. The film or covering (90) is folded such that it can allow for expansion of the stent (85) from its stent nonexpanded diameter (398) out to a stent expanded diameter (199) with a major axis distance (112) to meet the length of major axis of the channel (45) as shown in FIGS. 18C and 18D. The occlusion device (80) blocks blood flow through the stent lumen (105) and hence blocks blood flow through the channel (45). The release of such an occlusion device (80) is similar to that describe for other embodiments that use an outer sheath to deliver the occlusion device; removal of the sheath allows for expansion of the occlusion device (80) within the channel (45).

The SE stent (85) of the SE occlusion device (80) can have bulbous ends (400) on the proximal and distal ends (130) of the stent (85) with a larger bulb diameter (405) than the stent major axis distance (112) or stent minor axis distance (118) in the central region (355) of the stent as shown in FIGS. 19A-19C. Upon release of the covered stent (85) from the external sheath the bulbous regions expand outwards on each end of the channel (45) to further reduce the possibility for migration of the occlusion device (80) within the channel (45). The bulbous ends are thermally formed into the elastomeric metal (or polymeric or composite) stent (85) such that they have an equilibrium bulb diameter (405) upon expansion that is larger than either the stent major axis distance (112) or stent minor axis distance (118) of the central region (355) of the stent. The bulbous ends have a bulb diameter (405) that is 10% (range 5-20%) larger than either the major axis distance (112) or stent minor axis distance (118) and does not interfere with the function of the replacement leaflets found in the stent valve.

Figure 20B:
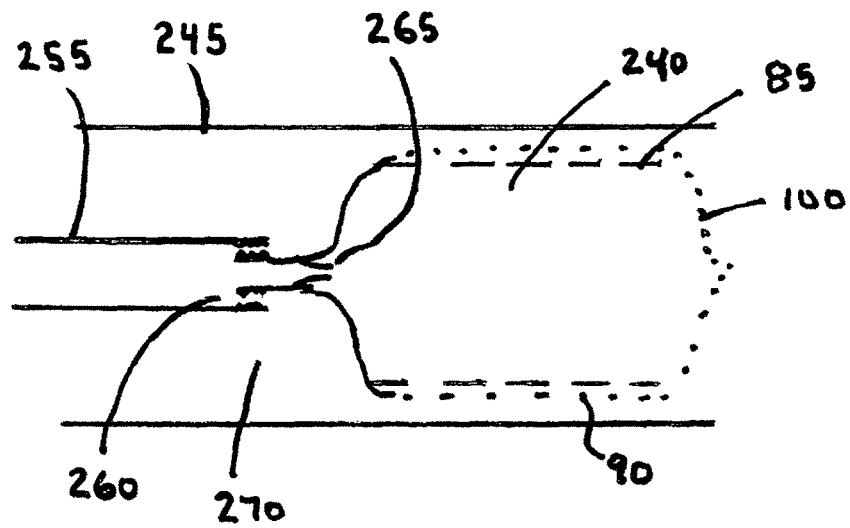
FIG. 20B is a self-expanding over the wire occlusion device that also has a dilation balloon to ensure full dilation of the stent.
Figure 20A:
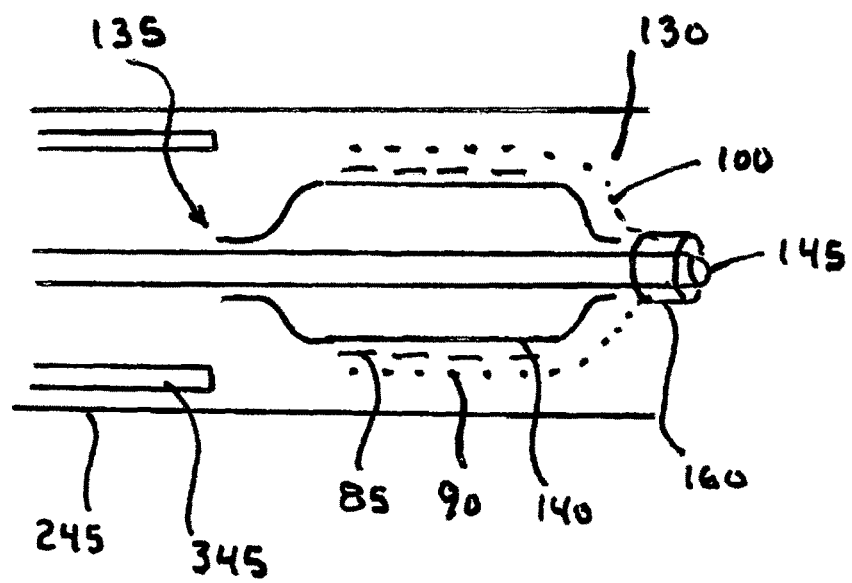
FIG. 20A is an balloon expandable occlusion device that has a distal blocking cover and that is delivered from an external sheath.

An additional embodiment for the SE occlusion device (80) of the present invention is shown in FIG. 20A. In this embodiment a SE stent (85) with a covering (90) and having a closed covering (100) located at the distal end (130) of the occlusion device (80) is positioned over an expandable balloon (140) that is positioned at the distal end of a balloon catheter. The expandable balloon (140) is an elastomeric balloon as described earlier for embodiments of the balloon expandable (BE) occlusion device. The expandable balloon (140) can be formed from silicone, polyurethane, or other elastomeric polymer, copolymer, or composite material. The occlusion device (80) is collapsed into its smaller diameter delivery configuration and held by an external sheath. The guidewire tubing for the balloon catheter (135) extends through the closed covering (100) at the distal end (130) of the occlusion device (80) and a flapper valve (160) as describe earlier allows the opening for the guidewire tube (145) through the flapper valve (160) to close upon removal of the balloon catheter. Alternately, the closed covering (100) can close via elastic contraction without the need for a flapper valve. The device is delivered OTW across the channel (45) wherein the sheath is removed allowing expansion of the SE stent (85) into the channel (45). The balloon is then expanded within the SE stent (85) to further dilate the occlusion device (80) and place it into better approximation with the channel (45) wall. The expandable balloon (140) is then deflated and the balloon catheter (135) is removed. The SE occlusion device (80) is left in place within the channel (45) making good approximation into the undulations (78) found in the channel (45) and having little chance for migration out of the channel (45).

A further embodiment for the SE occlusion device (80) of the present invention has a SE stent (85) contained completely within an occlusion balloon (240) (or attached to an occlusion balloon) which serves as a covering (90) for the occlusion device (80) as well as a blocking fabric (100) for the occlusion device; the balloon is formed from a noncompliant material having a diameter that is at least as large as the diameter of the major axis of the channel (45) (see FIG. 20B). The proximal end (270) of the balloon has a threaded attachment to a delivery tube (255) or other attachment mechanisms or holding assembly (255). The balloon-covered SE stent (85) is held into a small diameter delivery configuration via an external sheath. The device is delivered to the channel (45) via the external sheath. The device is held by the delivery tube (255) while the sheath is withdrawn allowing the SE stent (85) to expand outwards into contact with the channel (45). Next the delivery tube (255) used to inflate the balloon with either saline or curable polymer. A duckbill valve or check valve located near the proximal end (270) of the balloon ensures that the saline or polymer does not escape through the proximal end (270) of the balloon. The check valve can be eliminated, if desired, from this embodiment to allow saline inflation fluid to flow out of the balloon following delivery of the occlusion device (80) to the channel (45).

The embodiments presented in this specification are not intended to limit the scope of the present invention. Reference numerals used in the present specification for an embodiment of the present invention are intended to apply to other embodiments of the present invention.

The invention claimed is:

1. An occlusion device for occluding a perivalvular leak channel located along the perimeter of an implanted valve of the heart, said occlusion device comprising;
   A. an occlusion balloon having a first element of a holding assembly located at a proximal end of said occlusion balloon, said proximal end of said occlusion balloon having an open orifice,
   B. a stent permanently attached to said occlusion balloon, said occlusion balloon serving as a covering to prevent blood flow through a lumen of said stent in an expanded configuration,
   C. a delivery tube having a second element of said holding assembly located at a distal end of said delivery tube, said second element of said holding assembly being attachable to said first element of said holding assembly, said holding assembly holding said occlusion balloon into a sealing contact with said delivery tube for delivery of inflation fluid to said occlusion balloon to provide said occlusion balloon with an inflated volume, said first element of said holding assembly being detachable from said second element of said holding assembly,
   D. said occlusion balloon able to provide passage for unrestricted removal of said inflated volume out of said open orifice with said occlusion balloon detached from said delivery tube after said occlusion balloon has been inflated within the perivalvular leak channel and detached from said delivery tube with said stent remaining in said expanded configuration.

2. The occlusion device of claim 1 wherein said occlusion balloon is formed from an elastic material having an areal strain capability of at least 200%.

3. The occlusion device of claim 1 wherein said stent is formed from a balloon expandable material.

4. The occlusion device of claim 1 wherein said stent has hinges in bent regions and struts providing linear elements connecting said hinges; said hinges having a hinge width that is less than a strut width of said struts.

5. The occlusion device of claim 4 wherein said hinges having a hinge radial dimension that is greater than a strut radial dimension of said struts.

6. The occlusion device of claim 4 wherein said hinges are formed from a plastically deformable material and said struts are formed from a self-expanding material.

7. The occlusion device of claim 4 wherein said hinges and said struts are formed from a plastically deformable material.

8. The occlusion device of claim 4 wherein said hinges and said struts are formed from a self-expanding elastic material.

9. The occlusion device of claim 1 wherein said stent has hinges in bent regions and struts providing linear elements that join to said hinges, said hinges having a hinge radial dimension that is greater than a strut radial dimension of said struts.

10. The occlusion device of claim 1 wherein said holding assembly is fonued from a thread and screw mechanism.

11. The occlusion device of claim 1 wherein said holding assembly comprises a balloon stop located on said occlusion balloon and a member stop located on said delivery tube; said member stop having a larger diameter than said balloon stop during attachment of said occlusion balloon to said delivery tube; said member stop having a smaller diameter than said balloon stop during detachment of said occlusion balloon from said delivery tube.

12. The occlusion device of claim 1 wherein said occlusion balloon has a slidable seal located at a distal end of said occlusion balloon, said slidable seal providing for passage of a guidewire therethrough, said slidable seal preventing substantial leakage of inflation fluid out of said occlusion balloon during inflation of said occlusion balloon with inflation fluid.

13. An occlusion device for occluding a perivalvular leak channel located along the perimeter of an implanted valve of the heart, said occlusion device comprising;
- A. an occlusion balloon having a first element of a holding assembly located at a proximal end of said occlusion balloon, said proximal end of said occlusion balloon having an open orifice,
- B. a stent attached to said occlusion balloon, said occlusion balloon serving as a covering to prevent blood flow through a lumen of said stent in an expanded configuration,
- C. a delivery tube having a second element of said holding assembly located at a distal end of said delivery tube, said second element of said holding assembly being attachable to said first element of said holding assembly, said holding assembly holding said occlusion balloon into a sealing contact with said delivery tube for delivery of inflation fluid to said occlusion balloon to provide said occlusion balloon with an inflated volume, said first element of said holding assembly being detachable from said second element of said holding assembly,
- D. said occlusion balloon able to provide passage for unrestricted removal of said inflated volume out of said open orifice with said occlusion balloon in a detached configuration that is detached from said delivery tube after said occlusion balloon has been inflated with the inflation fluid, said stent being attached to said occlusion balloon in said detached configuration with said stent in said expanded configuration.

* * * * *